(12) United States Patent
Kilbride et al.

(10) Patent No.: US 11,554,003 B2
(45) Date of Patent: Jan. 17, 2023

(54) FILTRATION DEVICES AND METHODS RELATED THERETO

(71) Applicant: The Regents of the University of California, Oakland, CA (US)

(72) Inventors: Bridget F. Kilbride, San Francisco, CA (US); Bradford R. H. Thorne, San Francisco, CA (US); Steven W. Hetts, Hillsborough, CA (US); Vitaliy Lvovich Rayz, Thiensville, WI (US)

(73) Assignee: The Regents of the University of California, Oakland, CA (US)

( * ) Notice: Subject to any disclaimer, the term of this patent is extended or adjusted under 35 U.S.C. 154(b) by 1216 days.

(21) Appl. No.: 15/751,603

(22) PCT Filed: Aug. 11, 2016

(86) PCT No.: PCT/US2016/046640
§ 371 (c)(1),
(2) Date: Feb. 9, 2018

(87) PCT Pub. No.: WO2017/027754
PCT Pub. Date: Feb. 16, 2017

(65) Prior Publication Data
US 2020/0139039 A1    May 7, 2020

Related U.S. Application Data

(60) Provisional application No. 62/204,374, filed on Aug. 12, 2015.

(51) Int. Cl.
*A61F 2/01* (2006.01)
*A61M 1/36* (2006.01)

(52) U.S. Cl.
CPC ............. *A61F 2/01* (2013.01); *A61M 1/3615* (2014.02); *A61M 1/3687* (2013.01)

(58) Field of Classification Search
CPC ..... A61M 1/3615; A61M 1/3687; A61F 2/01; A61B 2017/00871; A61B 2017/00893
See application file for complete search history.

(56) References Cited

U.S. PATENT DOCUMENTS

| | | | |
|---|---|---|---|
| 2002/0165575 A1* | 11/2002 | Saleh | A61B 5/076 606/200 |
| 2010/0274277 A1 | 10/2010 | Eaton | |
| 2011/0082412 A1 | 4/2011 | Hyde et al. | |
| 2011/0190863 A1 | 8/2011 | Ostroot et al. | |
| 2011/0282274 A1 | 11/2011 | Fulton, III | |
| 2015/0305850 A1* | 10/2015 | Hetts | A61M 1/3615 606/200 |

FOREIGN PATENT DOCUMENTS

WO    2014/100201    6/2014

* cited by examiner

*Primary Examiner* — Benjamin J Klein
(74) *Attorney, Agent, or Firm* — Thomas | Horstemeyer, LLP

(57) ABSTRACT

In vivo and ex vivo positionable filtration devices are provided that are functionalized to bind one or more therapeutic agents in blood flowing in a blood vessel.

40 Claims, 21 Drawing Sheets

FIG. 3A
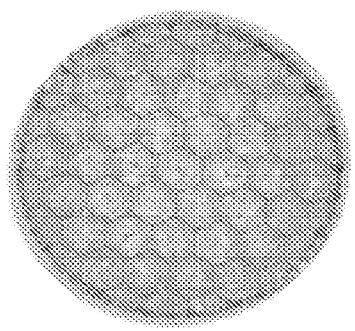
FIG. 3B
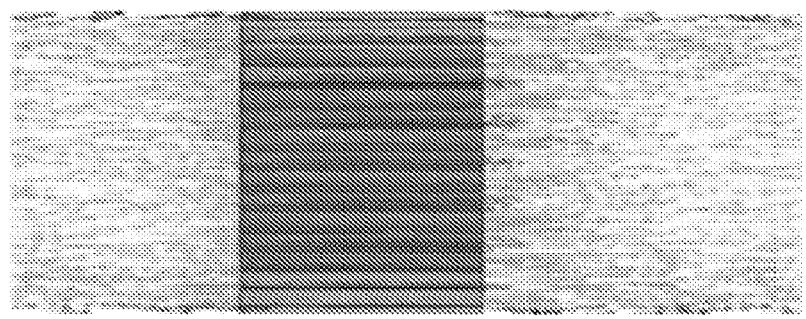
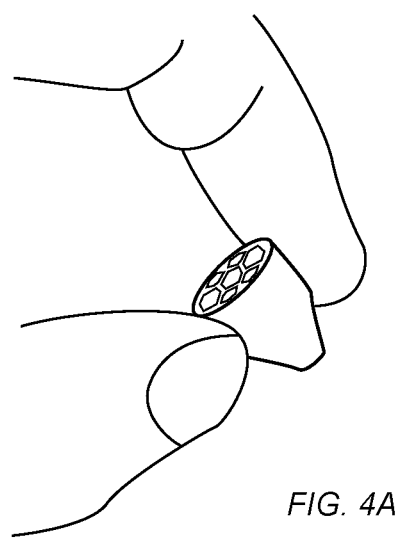
FIG. 4A

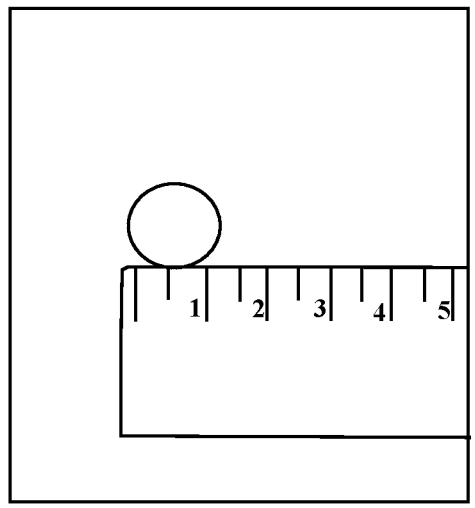
FIG. 7
FIG. 8A
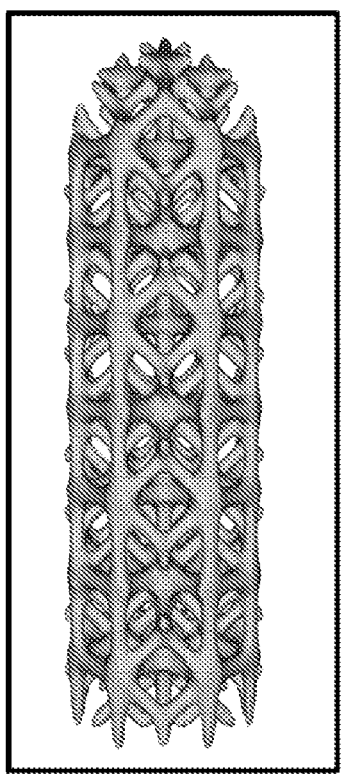
FIG. 8B
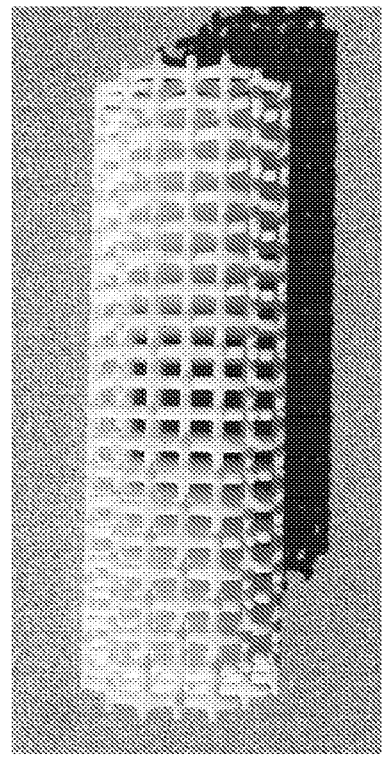

FILTRATION DEVICES AND METHODS RELATED THERETO

CROSS REFERENCE TO RELATED APPLICATIONS

This application claims the benefit of U.S. Provisional Application No. 62/204,374, filed Aug. 12, 2015 which application is incorporated herein by reference in their entirety.

STATEMENT REGARDING FEDERALLY SPONSORED RESEARCH

This invention was made with government support under grant no. R01 CA194533, awarded by the National Institutes of Health. The government has certain rights in the invention.

INTRODUCTION

Dosing of drugs ranging from cancer chemotherapeutics to anti-microbials to thrombolytics is currently limited by systemic side effects. During localized drug therapy, excess drug that is not immediately trapped in the target tissue passes through the organ's draining veins, then into the systemic circulation, and then to the rest of the body where it causes systemic toxicities. As such, it is desirable to develop endovascular medical devices that remove specific drugs from the blood stream in order to reduce systemic toxicities.

SUMMARY OF THE INVENTION

In some aspects of the present disclosure, in vivo positionable filtration devices are provided for filtering one or more therapeutic agents in blood flowing in a blood vessel. In some embodiments, the filtration device includes an elongated member dimensioned for positioning within a blood vessel of a human or non-human animal and to allow blood to flow through an interior of the filtration device, and where a surface of the filtration device is functionalized to bind one or more therapeutic agent in the blood.

In some aspects of the present disclosure, methods of in vivo filtration of a therapeutic agent are provided. In some embodiments, the method includes positioning a filtration device as described herein in a blood vessel of a body of a human or non-human animal, the filtration device positioned downstream from a target tissue site, the filtration device for binding a therapeutic agent in the blood flowing in the blood vessel, and administering the therapeutic agent upstream from the target tissue site to direct flow of the therapeutic agent to the target tissue site and then to the filtration device, where the in vivo positioned filtration device binds the therapeutic agent as the blood and the therapeutic agent traverse through the filtration device.

In still further aspects of the present disclosure, methods of ex vivo filtration of a therapeutic agent are provided. In some embodiments, the method includes connecting a filtration device as described herein in fluid communication with a blood vessel of a body of a human or non-human animal at a connection point downstream from a target tissue site for filtering the therapeutic agent in the blood flowing in the blood vessel, administering a therapeutic agent upstream from the target tissue site to direct flow of the therapeutic agent to the target tissue site and then to the filtration device, assisting the blood to flow ex vivo and contact the ex vivo filtration device, such that the filtration device binds the therapeutic agent as the blood and the therapeutic agent are received by the filtration device, and assisting the filtered blood to flow back into the blood vessel of the body of the human or non-human animal.

These and other objects, advantages, and features of the invention will become apparent to those persons skilled in the art upon reading the details of the invention as more fully described below.

In certain embodiments, a filtration device for filtering one or more therapeutic agents in blood flowing in a blood vessel. The filtration device may include a solid elongated member; at least one channel or a plurality of channels formed in the solid elongated member, wherein the channel(s) extends along a longitudinal axis of the solid elongated member; wherein the filtration device is dimensioned for positioning within a blood vessel of a human or non-human animal; and wherein the filtration device comprises a surface functionalized to bind to a therapeutic agent in blood flowing through the filtration device.

In certain embodiments, the solid elongated member comprises a cylindrical member comprising a frustoconical leading edge opposite a planar edge; a plurality of channels formed in the solid elongated member, wherein the channels extend from the frustoconical leading edge to the planar edge.

In certain embodiments, the solid elongated member is a cylindrical member comprising a first planar edge opposite a second planar edge and a plurality of channels extending from the first planar edge to the second planar edge.

In certain embodiments, a channel of the plurality of channels is located in the center of the device and remaining plurality of channels are arranged concentrically around the central channel.

In certain embodiments, the plurality of channels are (i) parallel to each other, (ii) extend along a non-linear path between the ends of the device, (iii) extend along a linear path between the ends of the device and are not parallel to each other.

In certain embodiments, the plurality of channels are parallel to a longitudinal axis of the device, the longitudinal axis extending from the frustoconical leading edge to the planar edge.

In certain embodiments, the cylindrical member is dimensioned to (a) fill a cross-section of the blood vessel, (b) have a diameter smaller than the blood vessel diameter, or (c) have a diameter larger than the blood vessel diameter.

In certain embodiments, a surface of the filtration device at one or more edge and/or a surface of the plurality of channels of the device is functionalized to bind to a first therapeutic agent or to a plurality of therapeutic agents.

In certain embodiments, the plurality of channels include a circular or an oval shaped opening at an edge of the device. In certain embodiments, the plurality of channels comprise a hexagonal opening at an edge of the device. In certain embodiments, the periphery of the plurality of channels comprise a hexagonal shape along the length of the channels. In certain embodiments, the periphery of the plurality of channels comprise a cylindrical shape along the length of the channels.

In certain embodiments, the outer surface of the device and/or the interior surface of the channels is functionalized with a moiety for binding to a first therapeutic agent. In certain embodiments, the outer surface of the device and/or the interior surface of the channels is functionalized with a plurality of moieties for binding to a plurality of therapeutic agents.

In certain embodiments, the solid elongated member comprises a cylindrical member comprising a frustoconical leading edge opposite a planar edge; a plurality of channels formed in the solid elongated member, wherein the channels extend from the frustoconical leading edge to the planar edge, wherein the filtration device is positioned in the blood vessel such that the blood enters the filtration device at the frustoconical leading edge and exits the device at the planar edge.

In certain embodiments, the cylindrical member is dimensioned to fill a cross-section of the blood vessel where a longitudinal axis extending from the frustoconical leading edge to the planar edge of the device is parallel to the direction of flow of blood in the blood vessel such that the blood traverses through the channels of the device.

In certain embodiments, the filtration device for filtering one or more therapeutic agents in blood flowing in a blood vessel may include a hollow elongated member comprising a circular shape along an axis perpendicular to a longitudinal axis of the member and a first circular open end opposite a second circular open end; a plurality of structures disposed inside the hollow elongated member, wherein the plurality of structures increase surface area of the device and decrease rate of blood flow through the device, wherein a surface of the device is functionalized for binding to the therapeutic agent in the blood flowing through the device, and wherein the filtration device is dimensioned for positioning within a blood vessel of a human or non-human animal. In certain embodiments, the structures are two-dimensional or three-dimensional and are disposed at an angle perpendicular to a longitudinal axis of the device.

In certain embodiments, the filtration device for filtering one or more therapeutic agents in blood flowing in a blood vessel may include a hollow elongated member comprising a first open circular end opposite a second open circular end and a network of cavities located in the interior of the hollow elongated member; a plurality of openings located along an outer surface of the cylindrical member, wherein the plurality of openings are connected to the network of cavities, wherein a surface of the device is functionalized for binding to a therapeutic agent in the blood flowing through the plurality of channels, and wherein the filtration device is dimensioned for positioning within a blood vessel of a human or non-human animal. In certain embodiments, the filtration device comprises a lattice formed from a biocompatible polymer. In certain embodiments, a surface in interior of the filtration device is functionalized for binding to the therapeutic agent. In certain embodiments, the filtration device is dimensioned such that an outer surface of the filtration device is in contact with the inner wall of the blood vessel in which the filtration device is positioned. In certain embodiments, the device is cylindrical in shape.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIGS. 3A and 3B illustrate simulated flow of blood through a filtration device having a plurality of honey-comb, hexagonal-shaped channels. FIG. 3A is a cross sectional view and FIG. 3B is a side-view of the device showing velocity of blood flow across the device through the different channels.

FIGS. 4A and 4B illustrate a side view and a top view, respectively, of a poly(vinyl alcohol) (PVA)-casted scaffold based on the digital rendering in FIGS. 1A and 1B.

FIGS. 5-7 illustrate various PVA-casted scaffold geometries of exemplary filtration devices.

FIGS. 8A and 8B illustrate a digital rendering of a castable lattice scaffold and the associated 3D-printed positive, respectively.

FIG. 18A, the openings in the filtration device are randomly arranged to provide a dense network of cavities. FIG. 18B, the openings in the filtration device are randomly arranged to provide a less dense network of cavities. The openings in the lattice of the device in FIG. 18A are smaller than the openings in the lattice of the device in FIG. 18B.

In FIG. 19B, the cells in the lattice decrease in size from one end on the device to the other end.

FIG. 23A shows the filtration device with the turbine-like inner blades which oriented in same direction. FIG. 23B shows alternating that the number of blades alternate between more blades in a first cross section of the device with less blades in the next cross section of the device. FIG. 23C shows a side-view of the device pictured in FIGS. 23A and 23B. The blades at each level are oriented at a 15 degree offset from the blades at the previous level. FIG. 23D is a cross-sectional front view of the device from FIGS. 23A-23C showing the blades at that cross-section. FIG. 23E is a cross-sectional front view of the device from FIGS. 23A-23D showing blades at multiple levels.

FIG. 24A is a cross-sectional front view of the device. FIG. 24B is a cross-sectional front view of the device, showing multiple levels. FIG. 24C is an oblique view of the device shown in FIGS. 24A and 24B. FIG. 24D is an oblique view of the device pictured in FIGS. 24A-24B, showing multiple levels. FIG. 24E is a side view of the device, showing the convex leading edge on the left.

FIG. 25B shows an oblique view of the vents in the filtration device where the vent-like channels traverse the entire device in a helical fashion. FIG. 25C is a transparent oblique view of the device shown in FIG. 25C, showing the channels traversing the device in a helical fashion. FIG. 25D is a transparent side view of the device shown in FIG. 25B.

DETAILED DESCRIPTION OF THE INVENTION

Figure 1A:
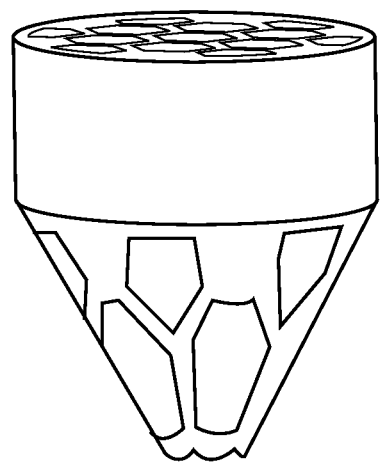
FIGS. 1A and 1B illustrate a side view and a top view, respectively, of a polymeric scaffold digital rendering of an exemplary filtration device.

Before the present devices and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which the devices and methods disclosed herein belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a device" includes a plurality of such devices and reference to "the compound" includes reference to one or more compounds and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Filtration Devices

Dosing of drugs is generally limited by systemic toxic side effects. Intraarterial chemotherapy (IAC) permits delivery of therapeutics at high concentration to a target organ, but systemic toxicities often still limit dosing when the therapeutic agent exits the target organ via venous drainage. Described herein is a new class of image-guided temporarily deployed in vivo, e.g., endovascular, filtration devices that selectively remove specific therapeutic agents from the blood stream in situ in order to reduce systemic toxicities and thereby increase the safety and efficacy of locoregional drug therapy.

Filtration devices described herein are elongate three-dimensional structures, the surface area of which is functionalized to bind and retain a therapeutic agent in the blood as the blood contacts the surface of the filtration device. The filtration devices of the present disclosure may adapt any three-dimensional shape that increases the surface area that comes in contact with the blood in the blood vessel where the device is positioned. In addition, the dimensions of the device are configured based upon the features of the blood vessel in which the device is to be deployed. For example, the length of the device can be determined by the length of the blood vessel where the device is to be positioned. A longer blood vessel can accommodate a longer device, while for positioning in a shorter blood vessel the device length may be decreased. Similarly, the width (e.g., the diameter for a device having a circular cross-section) of the device may be determined by the width of the blood vessel at which the device is to be positioned as well as the degree of fit inside the blood vessel. For example, when a tight fit is desired, the diameter of the device can be longer than that of the blood vessel. In other embodiments, the diameter of the device may be dimensioned to have a snug fit inside the lumen of the blood vessel without causing dilation of the blood vessel. In some embodiments, the diameter of the device may be smaller than the diameter of the blood vessel lumen where the device is positioned. In such an embodiment, the device may be tethered in place using a tethering device, such as, a catheter.

In some embodiments, the filtration device may be elongate with a circular cross-section (which is perpendicular to the longitudinal axis of the device extending from one end to the opposite end) where the diameter of the device decreases from one end to the opposite end of the device. The ends of the device may be planar (flat), pointed into or out of the device (concave or convex) and may have a pointed end or a curved end. In some embodiments, the filtration device may be generally cylindrical in shape. The cylindrical shape may extend from the distal end to the proximal end of the filtration device or in some cases the cylindrical shape may be limited to the distal end or the proximal end of the filtration device. For example, in certain cases, the filtration device may be cylindrical at the proximal end and tapered into a frustoconical or a conical shape at the distal end. In these cases, the transition from a cylindrical shape into a tapered shape may start at the distal end, at a location close to the distal end, or at a location closer to the proximal end.

References may be made herein to a proximal and distal end of the filtration device or components therein. The term "proximal" is used here to refer generally to the end or side of the filtration device or component thereof that is closer to the operator of the device (e.g., physician) than to the target tissue. The term "distal" is used here to refer generally to the end or side of the filtration device or component thereof that is closer to the target tissue site than to the operator of the device. As such, a leading edge of a filtration device is the distal edge/end and is closer to the target tissue site and is the edge at which the blood enters the filtration device.

In certain embodiments, the filtration device may be a solid device comprising an outer wall extending between the distal and proximal ends of the device which outer wall is free of any pores, holes, or openings that would allow blood to traverse into the interior of the device. However, the distal and proximal ends of the device may include at least one opening connected to a channel in the interior of the device that allows blood to enter the device at the distal end of the device and exit at a proximal end of the device. The distal end may be planar, conical, frustoconical, or convex in shape and may include an opening connected to the channel. The proximal end of the device may have any shape, e.g., planar, conical, frustoconical, convex, or concave and may include an opening connected to the channel. The overall shape of the filtration device may be any of the shapes described herein. In certain embodiments, the distal and proximal ends may have a plurality of openings connecting to a plurality of channels in the interior of the device. In certain embodiments, the outer wall may be smooth and devoid of any structures. For example, the outer wall of the filtration device may be substantially smooth and the device may be dimensioned such that the outer wall contacts the inner wall of the blood vessel in which the filtration device is positioned. In certain embodiments, the outer wall of the filtration device may include indentations that allow for blood to traverse through an area between the outer wall of the filtration device and inner wall of the blood vessel. The indentations may be placed uniformly, for example, separated by a defined distance. The indentations may extend between the distal end and the proximal end of the filtration device in a straight line or a curved line.

In certain embodiments, the filtration device may include a solid scaffold with a through-hole or a channel that extends from the distal end to the proximal end of the device and is dimensioned to allow for flow of blood when the filtration device is positioned in vivo in a blood vessel. The channel may be located in the center of the device or may be off-center. In certain embodiments, the filtration device may include a plurality of through-holes or channels that extend from the distal end to the proximal end of the device and are dimensioned to allow for flow of blood when the filtration device is positioned in vivo in a blood vessel. The channels may extend in a straight line through the interior of the filtration device or along a curved line. The plurality of channels may intersect each other in the interior of the filtration device forming a network of channels. In certain embodiments, the plurality of channels may not intersect each other. In certain embodiments, the plurality of channels may be spaced apart uniformly in a particular shape, such as, placed concentrically around the center of the filtration device. A channel may also be included in the center of the filtration device. In other embodiments, the channels may be placed in a spiral fashion. In some embodiments, the filtration device may include more channels in a central area of the filtration device and fewer channels closer to the periphery of the device. The overall shape of the filtration device may be any of the shapes described herein. It is understood that certain aspects from the different embodiments of the filtration devices may be combined to provide a device that includes a combination of the aspects in a single device.

In some embodiments, the filtration device may include a hollow scaffold where the distal end and/or proximal end of the filtration device is open and provides access to the interior of the filtration device. The outer wall of the device extending from the distal end to the proximal end may be a continuous wall devoid of any pores, holes, openings, and the like that permit blood to enter the device therethrough. The overall shape of the filtration device may be any of the shapes described herein. The interior of the filtration device is partially occupied by structures that increase the surface area of the device exposed to blood inside the device. The structures may be placed across the interior lumen of the filtration device and may extend from a location on an inner wall of the device to another location on the inner wall. The structures may be two-dimensional or three-dimensional and may extend across the lumen of the filtration device parallel to each other. In certain embodiments, the structure may be arranged like blades in a turbine. In certain embodiments, the blades may be angled towards the distal end of the filtration device and may extend out from the cylindrical wall of the filtration device forming a convex shaped distal.

In certain embodiments, the filtration device of the present disclosure may be a hollow elongate device having a lattice outer wall extending between a proximal and distal ends of the device. The interior of the device may include a plurality of cavities defined by a lattice structure in the lumen of the device. Accordingly, the device may have an open distal and proximal ends and an outer wall with a plurality of openings. The lattice structure may be uniform in dimension or the cells of the lattice may decrease in dimension towards one end of the device.

The openings present within the filtration devices described herein may be of any shape, such as, circular, oval, honeycomb, diamond, square, rectangular, etc. The channels present within the filtration devices described herein may be of any shape, such as, cylindrical, semi-cylindrical, honeycomb, diamond, cube, cuboid, etc. The width of the openings and channels in the filtration devices described herein may be determined based on a number of factors, such as, desired rate of flow of blood through the device, the surface area of the device exposed to the blood, the blood pressure in the blood vessel where the device is to be positioned. For example, the width of the openings and channels may be larger in filtration devices placed in blood vessels is higher flow rate, while width of the openings and channels may be smaller in filtration devices placed in blood vessels is lower flow rate. In certain cases, the channels in the filtration device may be honeycomb shaped where a maximal surface area for exposure to the blood is desired. In some embodiments, the channels may have a non-uniform dimension, for example, the channels may be wider in certain sections and narrower in another section. The channels may extend straight through or along non-linear path. In some embodiments, the channels may be parallel to the longitudinal axis of the device. In some embodiments, the channels may be parallel to each other by at an angle to the longitudinal axis of the device. The width of the channels may range from 3 µm to 9 cm.

As noted above, the width and length of the filtration device may vary based on the blood vessel where it is to be positioned. In certain embodiments, the width of the filtration device matches the width of the blood vessel in which the device is to be positioned. In other embodiments, the width of the filtration device is smaller or larger than the width of the blood vessel in which the device is to be positioned. In certain embodiments, the filtration device may have a width up to 9 cm, for example, 5 µm-9 cm. In certain embodiments, the filtration device may have a width that is between 5 µm-5 cm, 5 µm-1 cm, 5 µm-5 mm, 5 µm-1 mm, 5 µm-0.5 mm, 5 µm-0.1 mm, 5 µm-50 µm, 5 µm-25 µm, 5 µm-10 µm, 10 µm-5 cm, 10 µm-1 cm, 5 mm-20 mm, 8 mm-15 mm, 8 mm-13 mm, 10 mm-13 mm, 10 µm-5 mm, 10 µm-1 mm, 10 µm-0.5 mm, 10 µm-0.1 mm, 10 µm-50 µm, 10 µm-25 µm, 25 µm-5 cm, 25 µm-1 cm, 25 µm-5 mm, 25 µm-1 mm, 25 µm-0.5 mm, 25 µm-0.1 mm, or 25 µm-50 µm, e.g., 5 µm, 10 µm, 25 µm, 50 µm, 0.1 mm, 0.5 mm, 1 mm, 5 mm, 1 cm, or 5 cm. In certain embodiments, a filtration device as provided herein may have any one of the foregoing widths and may have a length up to 30 cm, for example, 5 µm-30 cm. In certain embodiments, the filtration device may have a length that is between 5 µm-25 cm, 5 µm-20 cm, 5 µm-15 cm, 5 µm-10 cm, 5 µm-5 cm, 5 µm-1 cm, 5 µm-5 mm, 5 µm-1 mm, 5 µm-0.5 mm, 5 µm-0.1 mm, 5 µm-50 µm, 5 µm-25 µm, 5 µm-10 µm, 10 µm-25 cm, 10 µm-15 cm, 10 µm-10 cm, 10 µm-5 cm, 10 µm-1 cm, 10 µm-5 mm, 10 µm-1 mm, 10 µm-0.5 mm, 10 µm-0.1 mm, 10 µm-50 µm, 10 µm-25 µm, 25 µm-25 cm, 25 µm-15 cm, 25 µm-10 cm, 25 µm-5 cm, 25 µm-1 cm, 25 µm-5 mm, 25 µm-1 mm, 25 µm-0.5 mm, 25 µm-0.1 mm, or 25 µm-50 µm, e.g., 5 µm, 10 µm, 25 µm, 50 µm, 0.1 mm, 0.5 mm, 1 mm, 5 mm, 1 cm, 5 cm, 10 cm, 15 cm, 20 cm, or 25 cm.

In certain embodiments the device may be for placement in a small blood vessel such as a venule and may have a width of up to 30 µm, such as 5 µm-30 µm, 5 µm-25 µm, or 5 µm-20 µm. The length of this filtration device may be up to 1 mm, such as, between 5 µm-1 mm, 5 µm-0.5 mm, 5 µm-0.1 mm, 5 µm-50 µm, 5 µm-25 µm, or 5 µm-10 µm.

In certain embodiments the device may be for placement in a small vein and may have a width of up to 50 µm, such as, 5 µm-50 µm, 5 µm-25 µm, or 5 µm-10 µm. The length of this filtration device may be up to 3 mm, such as, 5 µm-3 mm, 5 µm-1 mm, 5 µm-0.5 mm, 5 µm-0.1 mm, 5 µm-50 µm, 5 µm-25 µm, or 5 µm-10 µm.

In certain embodiments the device may be for placement in a large vein and may have a width of up to 500 µm, such as, 5 µm-500 µm, 5 µm-250 µm, 5 µm-100 µm, 5 µm-50 µm, 5 µm-25 µm, or 5 µm-10 µm. The length of this filtration device may be up to 30 mm, such as, 5 µm-30 mm, 5 µm-20 mm, 5 µm-10 mm, 5 µm-1 mm, 5 µm-0.5 mm, 5 µm-0.1 mm, 5 µm-50 µm, 5 µm-25 µm, or 5 µm-10 µm.

In certain embodiments, the filtration device of the present disclosure may have a cylindrical member with a frustoconical edge opposite a planar edge. The device may include a plurality of circular or hexagonal channels extending between the planar and frustoconical edges. The openings of circular channels at the planar edge may be circular and the openings of the circular channels at the frustoconical edge may be oval. The openings of hexagonal channels at the planar edge may be hexagonal and the openings of the circular channels at the frustoconical edge may be hexagonal. It is evident that the openings to the channels on the frustoconical edge are wider compared to the openings on the planar edge due to the angle of the frustoconical edge. In certain embodiments, the diameter of the cylindrical portion of the device may be about 8 mm-20 mm, e.g., 10 mm-15 mm, or 10 mm-13 mm. The diameter or width of the channels (e.g., circular or hexagonal channels) may be 1 mm-5 mm, e.g., 1 mm-4 mm, 2 mm-4 mm, 2 mm-5 mm, 3 mm-5 mm, or 3 mm-4 mm. The channels may be parallel to the longitudinal axis extending centrally from the planar edge to the frustoconical edge of the device. The channels may be spaced apart from each other by any suitable distance determined by the diameter of the device and the number of channels. In certain cases, the channels may be a separated by a distance of 0.1 mm-2 mm, e.g., 0.1 mm-1 mm, 0.3 mm-1 mm, 0.4 mm-1 mm, 0.4 mm-0.8 mm, or 0.4 mm-0.6 mm. The length of the device from the planar edge to the end at the frustoconical edge may be 10 mm-30 mm, e.g., 10 mm-25 mm, 10 mm-20 mm, or 15-20 mm.

The widths of the devices as used herein refer to the widest cross-section of the device between the proximal and distal ends of the device. For a device have a circular cross-section, the width of the device refers to the diameter of the device. The widths listed herein provide the diameter at the widest cross section of the device. The length of the devices as used herein refers to the distance between the proximal and distal ends of the device. For filtration devices where the proximal and distal ends are non-planar in shape, the length of the device refers to the longest length between the proximal and distal ends of the device.

Figure 1B:
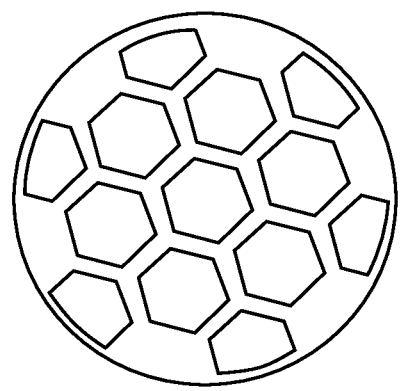

Exemplary filtration devices are provided in the accompanying figures. FIGS. 1A-1B illustrate a filtration device that include a solid cylindrical member comprising a tapered edge (a frustoconical leading edge) opposite a planar edge and hexagonal channels that provide for flow of blood through the interior of the device. The channels are honeycomb shaped. The honeycomb pattern increases the surface area of the filtration device in contact with blood and hence increases the surface area that binds to the therapeutic agent present in the blood. In use, the tapered end is the distal end of the device and is positioned such that blood contacts the tapered end before traversing through the filtration device. The channels extend straight through the device and are parallel to the longitudinal axis of the device. This device may be dimensioned to extend across the lumen of the blood vessel to force the blood to pass through the interior of the device or to have a smaller diameter than the lumen of the blood vessel to allow the blood to pass through the interior of the device as well around the exterior of the device.

Figure 2A:
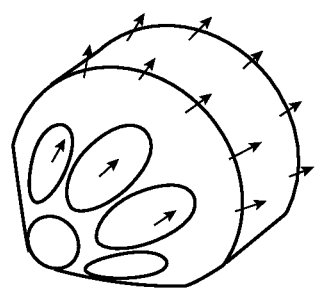
FIGS. 2A and 2B illustrate the simulated laminar flow through an exemplary filtration device depicted in FIGS. 1A and 1B.
Figure 2B:
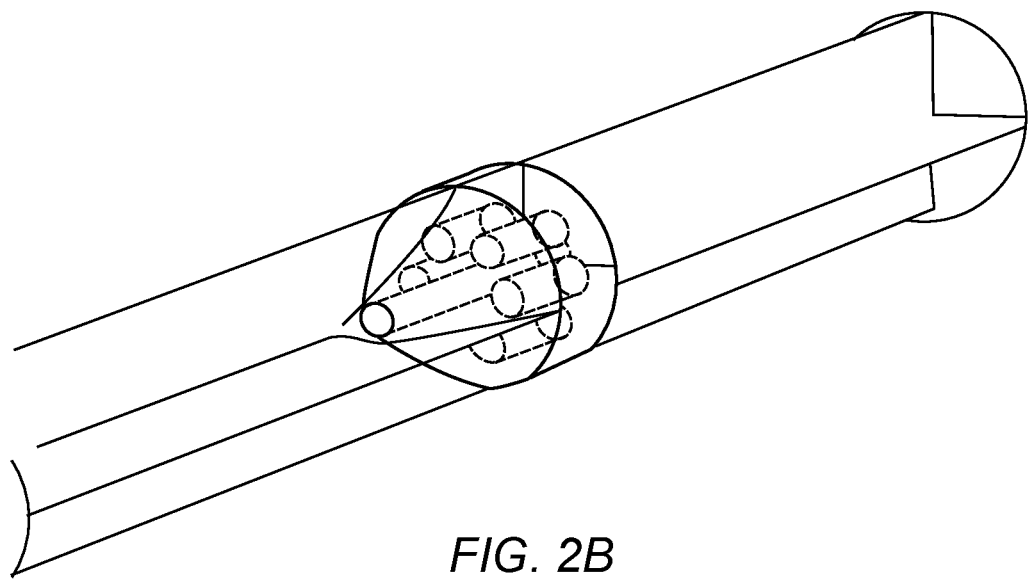

FIGS. 2A and 2B depict filtration devices that include a solid cylindrical member and a tapered end that includes channels that provide for flow of blood through the interior of the device. The channels are cylindrical and have a circular opening at the proximal end of the device and oval shaped opening at the distal end of the device. The centrally located channel has a circular opening at both ends. A simulated blood flow through the device shows that the tapered end facilitates flow of blood through the channels as well as around the periphery of the device. For blood flowing through the channels of the device, the centrally located channel provides the fastest flow rate. The channels extend straight through the device and are parallel to the longitudinal axis of the device.

FIG. 3A shows a cross-section of the device across an axis perpendicular to a longitudinal axis of the device. FIG. 3B shows a longitudinal cross-section of the filtration device. The filtration device is cylindrical with a plurality of honeycomb (hexagonal) shaped channels traversing therethrough along an axis parallel to the longitudinal axis of the device. In FIG. 3B, simulated blood flow is depicted showing that blood traverses through the channels in the central area of the device at a higher velocity than through the channels located towards the periphery of the device.

Figure 4B:
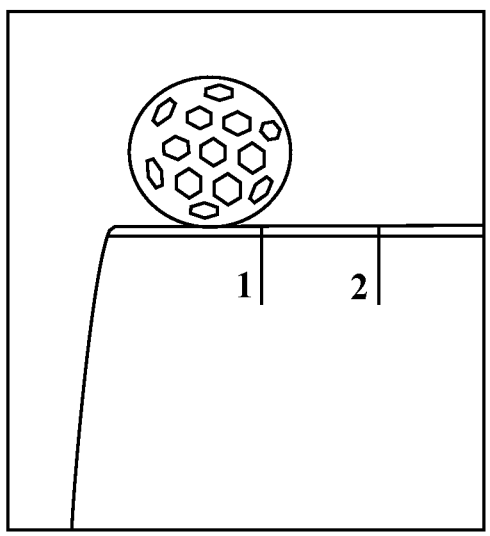

FIGS. 4A and 4B illustrate a side view and a top view, respectively, of a poly(vinyl alcohol) (PVA)-casted scaffold based on the digital rendering in FIGS. 1A and 1B. The device is 12.7 mm in diameter at the widest portion (i.e., the diameter of the cylindrical portion of the device) and is 16 mm cm in length (from the tip of the frustoconical leading edge to the planar edge). The channels are 3.175 mm in diameter with 0.5 mm between each channel.

Figure 5:
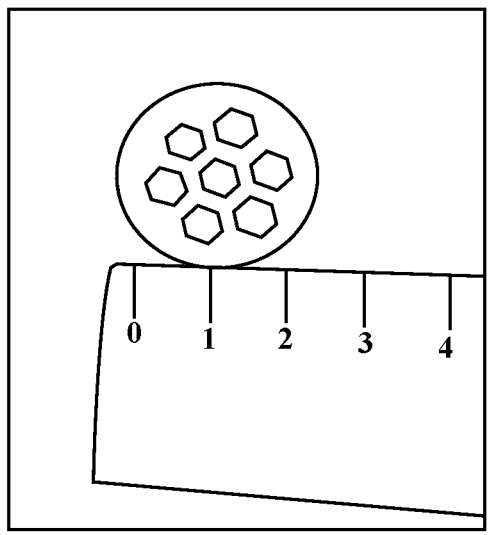
Figure 6:
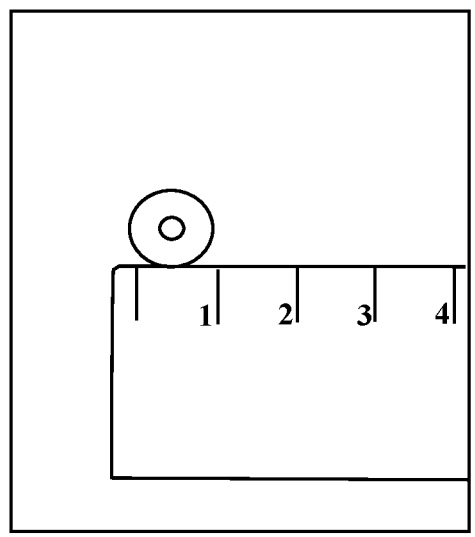
Figure 9A:
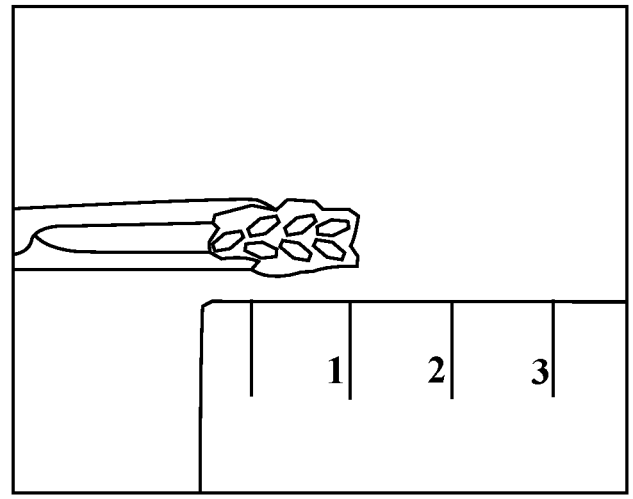
FIGS. 9A and 9B illustrate shape memory of the scaffold shown in FIGS. 4A and 4B during crude compression and after, respectively.
Figure 9B:
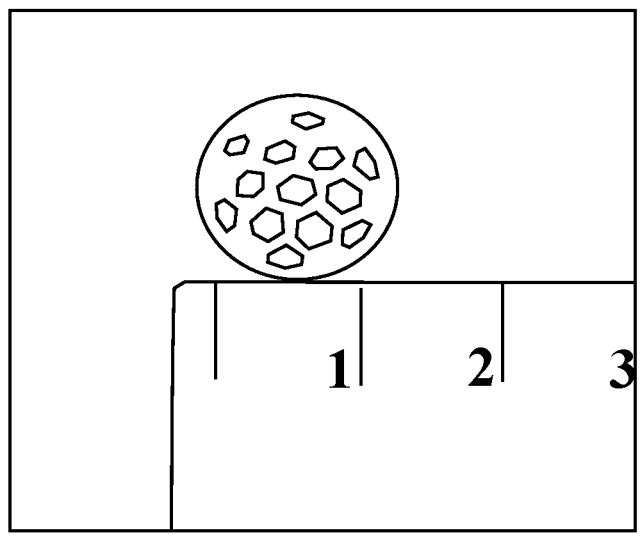
Figure 10A:
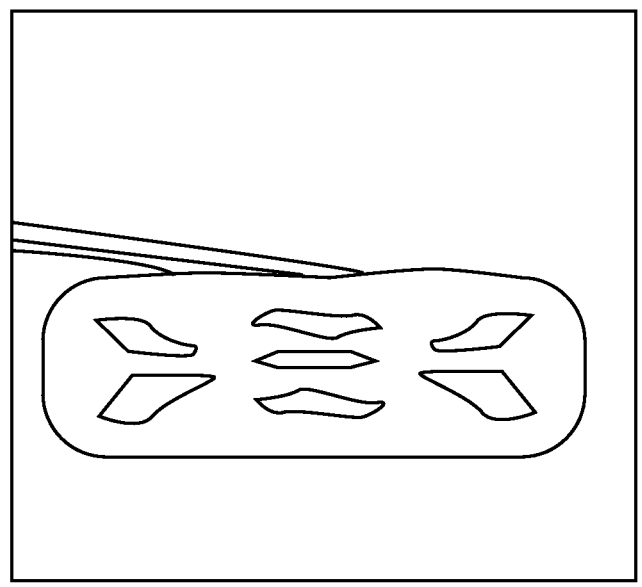
FIGS. 10A and 10B illustrate shape memory of the scaffold shown in FIG. 5 during crude compression and after, respectively.
Figure 10B:
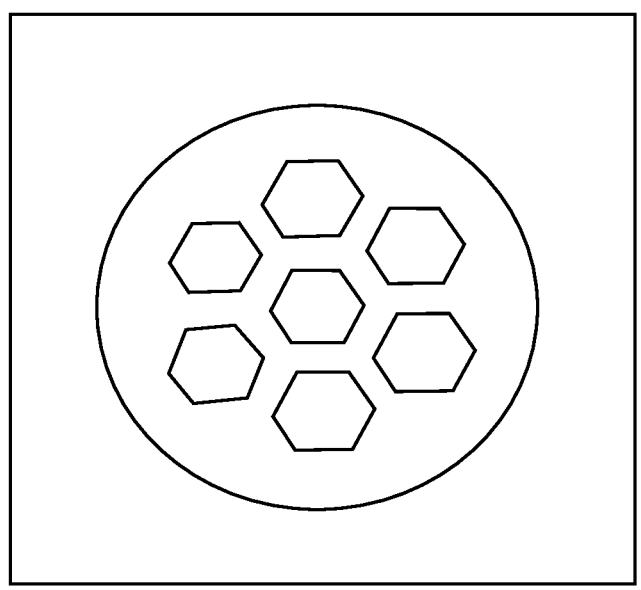

FIGS. 5-7 illustrate various PVA-casted scaffold geometries of exemplary filtration devices. In the device illustrated in FIG. 5, is a solid cylinder with a plurality of honeycomb shaped channels traversing through the device along an axis parallel to the longitudinal axis of the filtration device. The filtration device depicted in FIG. 6 includes a single channel. The filtration device depicted in FIG. 7 solid cylinder with no channels.

FIGS. 8A and 8B illustrate a digital rendering of a castable lattice scaffold and the associated 3D-printed positive, respectively. This device is hollow cylinder with a uniform lattice forming the wall of the device. Additional hollow filtration device having a lattice wall as well as lattice interior are shown in FIGS. 18A-18B and 19A-19B. The hollow filtration devices in FIGS. 18A-18B and 19A-19B have a circular cross section. The diameter of the device may stay constant throughout the length of the device or may change (e.g., decrease in diameter from one end to the opposite end). The device may be positioned in either orientation such that the blood flows along the longitudinal axis of the device. As is evident from these figures, blood may also enter and exits at the wall of the device.

Additional embodiments of filtration devices are depicted in FIGS. 20-25.

As is evident from the various filtration devices described herein, the filtration devices have a configuration to facilitate blood flow through and/or around the filtration device maximizing the surface area which is exposed to blood while minimizing the amount of resistance to the flow of blood. In certain embodiments, as noted above, the cross-sectional shape of the filtration device is dimensioned to occupy most if not all of the cross section of the blood vessel. Having the filtration device traverse the entire cross section of the blood vessel may ensure the most amount of blood and therapeutic agent enter the filtration device, and further may provide support or stability to retain the filtration device within the blood vessel. In some instances, the filtration device has a generally circular cross shape along at least one peripheral surface of the filtration device such as to conform to the generally circular cross shape of blood vessel.

The filtration devices of the present disclosure may be made using any biocompatible material. Exemplary materials include polymers. Any polymer material may be used to form the filtration devices disclosed herein. Representative polymers include polyvinyl alcohol (PVA), methacrylate polymers, polyethylene-imine and dextran sulfate, poly (vinylsiloxane) ecopolymerepolyethyleneimine, phosphorylcholine, poly(ethyl methacrylate), polyurethane, poly(ethylene glycol), poly(lactic-glycolic acid), hydroxyapetite, poly(lactic acid), polyhydroxyvalerte and copolymers, polyhydroxybutyrate and copolymers, polycaprolactone, polydiaxanone, polyanhydrides, polycyanocrylates, poly(amino acids), poly(orthoesters), polyesters, collagen, gelatin, cellulose polymers, chitosans, polystyrene divinylbenzene, hyaluronic acid-based materials and alginates or combinations thereof. It should be understood that various mixture of the polymers may be used.

Filtration devices described herein may be made using any suitable method or combination of methods, such as, using molds, 3-D printing, extrusion, filament deposition, laser sintering, thermal sintering, casting, photo-polymerization, laser-polymerization, temperature-induced polymerization, thermal cycling, cryo-polymerization, chemical crosslinking, physical crosslinking, stereolithography, chain-entanglement, and/or resin encapsulation.

In some embodiments, single or cyclic thermal modification may be used to modify mechanical properties of resulting polymeric scaffolds. Thermal cycling of PVA between cryogenic and ambient temperatures can yield improved mechanical stability and shape memory of the polymeric scaffold. Filtration devices in FIGS. 9A, 9B, 10A, and 10B illustrate super-elasticity and shape memory of thermally cycled PVA, post compression. In some embodiments, rigidity and mechanical stability of the polymeric scaffold may increase with a linear relationship to number of thermal cycles.

In certain embodiments, the filtration device may be derived from a negative image of an original master. For example, the liquid polymer may be used to fill the negative image. FIGS. 14-17 show example negatives for exemplary filter structures.

In alternative embodiments, the polymeric scaffold is formed through manufacturing techniques other than direct casting. For example, polymer may be deposited onto a surface to be bound or coated, temporary substrate, or other surface to form a film or membrane of same or similar binding or elution capabilities. Deposition of the polymer may be realized through but not limited to the following techniques: aerosol jet deposition, atomization, rolled, and/or scraped.

In certain embodiments, the polymeric scaffold may encapsulate, support, or otherwise bind a secondary polymer or resin. The secondary resin may share or differ in binding capabilities, target site, or target therapeutic. Polymeric scaffolds may include one or more non-primary polymers or resins depending on desired mechanism of operation. Different embodiments may express the primary polymeric scaffold as solid or porous depending on desired mode of operation. Example ion exchange resins may be found in U.S. Patent Publication No. US 2015-0305850, the entirety of which is incorporated herein by reference.

Environmental and atmospheric aspects may be controlled to adjust mechanical and chemical properties. In one embodiment, a partially-crosslinked polymer may be extruded onto a heated surface such that a polymeric scaffold is 3D-printed and crosslinked in tandem. In another embodiment, a partially-crosslinked polymer may be extruded onto a heated surface such that a polymeric scaffold and polymerized via UV light.

Filtration devices disclosed herein sequester therapeutic agents by binding to the therapeutic agents to remove excess therapeutic agents from the draining venous system during intra-arterial chemotherapy administration. Analogous to a central venous catheter or inferior vena cava filter, the filtration device of the present disclosure would be placed into the draining venous system, prior to an IAC infusion, would remain in place during IAC infusion, and would be removed from the body along with all of the captured therapeutic agents through its access sheath shortly following IAC. The filtration device may be positioned any suitable method, such as, image-guided insertion using, for example, x-ray fluoroscopic image guidance. In certain cases, the filtration device may be held in-place using a catheter, e.g., using a catheter used to position and deploy the filtration device in a blood vessel. In other cases, the filtration device may be held in-place inside a blood vessel without using a catheter. For example, a periphery of the filtration device may be sized to fit inside the blood vessel such that an outer surface of the filtration device is in contact with the inner wall of the blood vessel and the contact between the filtration device and the inner wall of the blood vessel holds the filtration device in place. In another embodiment, a periphery of the filtration device may be sized to have a diameter slightly larger than the diameter of the blood vessel. Placement of such a filtration device may introduce a slight expansion in the blood vessel and the tension from the blood vessel retracting back to its original diameter may hold the filtration device in the position at which it was deployed in the blood vessel.

In some embodiments, two or more filtration devices of interest may be inserted into a blood vessel and arranged in a series downstream of each other.

During locoregional intraarterial (IA) infusion of therapeutic agents (e.g., the chemotherapeutic doxorubicin), a significant fraction of the conjugated therapeutic particles pass through a targeted tumor into the veins draining the organ in which the tumor is located. Just prior to IA infusion of therapeutic agents, a filtration device is position in vivo, via, for example real time X-ray angiography guidance into the vein or veins draining the target organ. The filtration device then captures therapeutic agents passing through the target organ during immediately following IA infusion. Finally, the filtration device is removed from the patient after the IA infusion procedure, thus eliminating the therapeutic agents from the patient systemic circulation of the patient. This approach reduces systemic toxicity and thereby permits dose escalation during locoregional IA therapy. The filtration device may remain in the patient for a period of time sufficient to achieve the desired reduction in the level of the therapeutic agent in the blood of the patient following administration of the therapeutic agent. In certain embodiments, the filtration device may be removed after 1 min-10 days after the IA infusion procedure.

Although the overall approach of paired intraaterial infusion and venous filtration can theoretically be used for any drug or therapeutic agent, the most compelling initial application for this technology is increasing efficacy and safety of locoregional cancer chemotherapy. In certain embodiments, the filtration device is used in the treatment of patients with hepatocellular carcinoma (HCC). Image-guided transarterial chemoembolization (TACE), a form of IAC, is performed in IR and is a standard of care for unresectable primary and secondary hepatic malignancies. TACE increases survival compared to best supportive treatments in this population in a cost-effective manner. IAC is performed by navigating microcatheters into the arteries supplying tumors and directly delivering chemotherapy. In addition to treatment of HCC, IAC has been a successful palliative measure for thousands of patients with liver metastases and is of interest in cancers elsewhere in the body including infusion of nanoparticles to treat head and neck cancer. Doxorubicin (Dox) use is limited by systemic toxicities, consisting of bone marrow suppression, hair loss, gastrointestinal toxicity, and irreversible cardiac failure. Toxicity remains problematic in IAC since first pass hepatic clearance of Dox ranges from only 50-70% regardless of infused dose. Dox follows a therapeutic linear dose-response model, in which increasing dose linearly increases tumor cell kill, providing motivation for higher-dose Dox therapy.

The surface of the filtration device described herein is functionalized to bind to one or more therapeutic agents to be removed from the blood of a patient who has been administered the therapeutic agent(s). In some embodiments, at least a surface of the channels is functionalized. In other embodiments, an interior surface and an exterior surface of the filtration device is functionalized. In some embodiments, the entire surface of the filtration device is functionalized.

The nature of functionalization is selected based on the therapeutic agent to be removed from the blood. In certain embodiments, the functionalization may be chemical functionalization to bind to the therapeutic agent to be filtered out of the blood. In certain embodiments, a surface of the filtration device may be functionalized via sulphonation, carboxylation, or another chemical modification, such as a chemical modification to provide ion exchange capability, e.g., cation exchange capability. The functionalization may be carried out prior to or after formation of a scaffold of the filtration device. In certain embodiments, a solution of a pre-polymer may be reacted with a functionalization agent followed by polymerization of the solution, for example, into a scaffold of the filtration device. For example, an aqueous solution of poly(vinyl alcohol) (PVA) may be stirred and heated to form a homogenous solution. The resulting homogenous solution may be directly sulfonated through addition of varying amounts of sulfopthalic acid. The sulfonated PVA may then be chemically crosslinked with an aqueous solution of glutaraldehyde into a flexible, sulfonated material with ion exchange properties. In certain embodiments, a polymer may be functionalized as described in U.S. Patent Publication No. US 2015-0305850, which is incorporated herein by reference in their entirety.

In other embodiments, the functionalization of the filtration device includes bonding a chemical moiety that binds to a therapeutic agent. For example, the functionalization may include attaching a chemical moiety to the filtration device, which chemical moiety may be calsequestrin; cyclic oligosaccharide, e.g., cyclodextrins, including gamma-cyclodextrin; hNopp140; antibodies that specifically bind the therapeutic agent, such as an anti-doxorubicin monoclonal antibody (MAD 11); nucleolar phosphoprotein; *Clostridium botulinum* neurotoxin B; cell membrane lipids such as cardiolipin, phophatidylserine, and phosphatic acid; aptamers including RNA and DNA aptamers; albumin; and hemoglobin. The term "moiety" as used herein refers to any functional group that is able to bind to the surface of the filtration device or is incorporated into the filtration device (e.g., during the polymerization process) and is able to bind to the therapeutic agent directly or indirectly. In certain embodiments, a moiety may be present in the filtration device or may be bound to surface of the filtration device indirectly and may bind to the therapeutic agent directly. In other embodiments, a first moiety may be present in the filtration device or may be bound to surface of the filtration device indirectly (via a second moiety) and may bind to the therapeutic agent indirectly via a third moiety.

In certain embodiments, the filtration device may filter a therapeutic agent from the blood by inactivating or otherwise degrading the therapeutic agent or the toxicity of the therapeutic agent. For example, the filtration device may be a catalytic material, such as an immobilized (covalently or non-covalently) enzyme that, for example, enzymatically degrades the therapeutic agent to reduce its toxicity level. Enzymatic degradation and inactivation of Dox, for example, may occur via cleavage of its sugar backbone with glycosidases, such as, those contained in the liver.

In certain embodiments, the therapeutic agent administered to the patient may be pretreated by covalently or non-covalently associating the therapeutic agent with a magnetic particle, such as a magnetic nanoparticle. Accordingly, the filtration device may be functionalized with magnetic material so that following treatment the magnetically bound therapeutic particle may be attracted to the magnetic material of the filtration device.

In certain embodiments, the functionalization of the filtration device provides irreversible or weakly reversible binding to the therapeutic agent under physiological conditions. The amount of therapeutic agent removed from the blood by the filtration device may vary based on a number of factors, such as, the surface area of the filtration device functionalized to bind to the therapeutic agent, the rate of flow of blood across the filtration device, nature of the therapeutic agent, and filtration device configuration. In certain embodiments, the filtration devices of the present disclosure remove at least 10%, 20%, 30%, 40%, 50%, 60%, 70%, 80%, 85%, 90%, 95%, or more of the therapeutic agent from the blood, such as, at least 10%-100%, 15%-95%, 20%-90%, 25%-85%, 30%-80%, 30%-75%, 35%-70%, 40%-65%, or 40%-60%.

The reduction of the toxicity level may vary based on the selected filtration device, therapeutic agent, and specific filtration device configuration. In certain embodiments, the reduction of toxicity level ranges from 30%, 40%, 50%, 75%, 90% or greater as compared to toxicity level in absence of the filtration device.

In certain embodiments, the filtration devices of the present disclosure do not include beads, spheres, resins, or particles that are used in the art to adsorb and/or bind to a target agent. "Beads", "spheres", "resins", or "particles" refer to a substantially spherical particle such as a sphere or microsphere having a diameter in the range of 0.01 to 100 µm. The small size of these beads, spheres, resins, or particles necessitate use of mesh, membranes, bags, and the like to retain these inside a device if being used in vivo for filtration purposes. However, the shape of such a filtration device is not easily controlled. In certain embodiments, the filtration devices that are the subject of this patent application do not include beads, spheres, resins, or particles and further do not include mesh, membranes, bags, and the like needed to contain these beads, spheres, resins, or particles.

The filtration devices provided herein may include a material to improve biocompatibility, such as including but not limited to one or more of the following: PMMA, chitosan, heparin, citrate, and ethylenediaminetetraacetic acid (EDTA). For example, the filtration devices may include a coating of heparin, citrate, EDTA, or another anti-coagulant.

Therapeutic Agent

The therapeutic agent to be filtered out of the systemic blood circulation of a patient may include, for example, chemotherapeutic agents and/or non-chemotherapeutic agents. In one embodiment, the therapeutic agent is Dox and used to treat cancerous tissue, such as within an organ. Non-chemotherapeutic agents may include, but are not limited to, for example, anti-coagulants, thrombolytics (e.g., clot dissolving drugs such as tPA), vasoactive agents, e.g. verapamil, nicardipine, or milrinone; Sodium tetradecyl sulfate (Sotradecol, Angiodynamics or BioNiche Pharmaceuticals); bleomycin; X-ray or MRI contrast agents; antibiotics, etc. The thrombolytic may be used, for example, in stroke treatment. In certain embodiments, the therapeutic agent may be particles, such as drug eluting resins or polymers. Particles may include, for example, particles that occlude blood vessels of cancerous or otherwise diseased tissue. In some instances, particles may include polymers, glues, resins, activated carbon, or glass. In certain embodiments, the particles may be bound to radiation emitting isotopes, such as radiotherapeutic particles.

A chemotherapeutic agent may be an agent selected from the group consisting of S-phase dependent antimetabolics, capercitabine, cytarabine, doxorubicin, fludarabine, floxuridine, fluorouracil, gemcitabine, hydroxyurea, mercaptopurine, methotrexate, prednisone, procarbazine, thioguanine, M phase dependent vinca alkaloids, vinblastine, vincristine, vinorelbine, podophyllotoxins, etoposide, teniposide, taxanes, doxetaxel, paxlitaxel, G2-phase dependent, bleomycin, irinotecan, mitoxantrone, topotecan, G1-phase dependent, asparaginase, corticosteroids, alkylating agents, nitrogen mustards, mechlorethamine, mustargen, cyclophosphamide, ifosfamide and clorambucil, leukeran, nitrosoureas, platinum agents, cisplatin, platinol, carboplatin, paraplatin, antimetabolites, natural therapeutic products, antitumour antibiotics, anthracyclines, epipodophyllotoxins, vinca alkaloids, taxanes, camptothecin, melphalan, carmusline, methotrexate, 5-fluorouracil, mercaptopurine; daunorubicin; doxorubicin; epirubicin; vinblastine; vincristine; dactinomycin; mitomycin C; taxol; L-asparaginase; G-CSF; etoposide; colchicine; derferoxamine mesylate or a combination thereof.

The chemotherapeutic or radiotherapeutic agent may be associated with an antibody, for example a monoclonal antibody.

The therapeutic agent may include DNA, RNA, interfering RNA (RNAi), a peptide, polypeptide, an antibody for example a monoclonal antibody or an antibody fragment such as a single chain antibody fragment, an aptamer, a small molecule. Small molecules may include, but are not limited to, peptides, peptidomimetics (e.g. peptoids), amino acids, amino acid analogs, polynucleotides, polynucleotide analogs, nucleotides, nucleotide analogs, organic or inorganic compounds (i.e. including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Methods

In some aspects of the present disclosure, methods of in vivo and ex vivo filtration of one or more therapeutic agents are provided. The methods include positioning a filtration device in a blood vessel of a body of a human or non-human animal, and administering a therapeutic agent upstream from the target tissue site to direct flow of the therapeutic agent to the target tissue site and then to the filtration device positioned downstream from a target tissue site. For example, the filtration device may be positioned 5 mm or more downstream from the target tissue site, such as, 10 mm, 15 mm, 25 mm, 30 mm, 50 mm, 75 mm, 100 mm, 150 mm, 200 mm, 250 mm, 300 mm, 400 mm, 500 mm, 600 mm, 700 mm, 800 mm, 900 mm or more downstream from the target site. In certain embodiments, the filtration device is placed at a position ranging from 10 mm to 500 mm downstream from the target site, such as from 25 mm to 400 mm, such as from 30 mm to 300 mm, such as positioning the filtration device from 50 mm to 250 mm downstream from the target site. The in vivo positioned filtration device filters the therapeutic agent as the blood and the therapeutic agent are received by the filtration device. Various examples of blood vessels in which the filtration device may be positioned include the hepatic vein, iliac vein, inferior vena cava, renal vein, and superior vena cava. Additional exemplary sites for positioning of the present device also include, but are not limited to, intracranially in the dural venous sinuses (e.g., sigmoid sinus, transverse sinus, torcula, straight sinus, superior sagittal sinus) to remove agents during cerebral embolization or chemoinfusion; internal jugular vein with the device inserted, for example, either transfemorally or directly in the ipsilateral internal jugular vein, for head and neck tumors and during cerebral embolization or chemoinfusions; and the brachiocephalic vein between the superior vena cava and the internal jugular vein.

As used herein, the term "cancer" refers to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness. The term "cancer" includes malignancies of the various organ systems, such as those affecting, for example, lung, breast, thyroid, lymphoid, gastrointestinal, and genito-urinary tract, as well as adenocarcinomas which include malignancies such as most colon cancers, renal-cell carcinoma, prostate cancer and/or testicular tumours, non-small cell carcinoma of the lung, cancer of the small intestine and cancer of the esophagus. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head (including brain) and neck, colon, skin and ovary. The term "carcinoma" also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

It should be appreciated that the methods may include the filtration devices described in the present disclosure, and for the sake of clarity and brevity, will not be described in great detail again, but rather reference is made to the previous discussion of these features. Additionally, the description of the methods of using the filtration devices is also applicable to the methods section, and will not be described again great detail again but rather reference is made to the previous discussion.

The target tissue may include, for example, cancerous or otherwise diseased tissue. The target tissue site should be accessible by the bloodstream and may include organs for instance. Example cancerous tissue sites may include, but are not limited to the liver, kidney, brain, head/neck, skin gastrointestinal tract, and musculoskeletal system. For example, the target tissue site may include an organ afflicted with cancerous growths.

The therapeutic agent is administered upstream from the target tissue site—e.g., intraarterially or intravenously supplying a cancerous or otherwise diseased organ. In certain embodiments, the filtration device is positioned within a vein draining a target organ—e.g., an organ containing diseased or cancerous tissue—or a central vein. In some instances, for example, the filtration device may be inserted within an internal jugular or femoral vein. In some instances, the filtration device may be malleable to conform to the vein, such as the renal vein, hepatic vein, or vena cava.

The distance the filtration device is positioned from the target tissue site may vary based on the particular blood vessel, the location of the target tissue site (e.g., which organ), etc. The distance to the target tissue site or organ including the target tissue may vary. For instance, example distances may include, but are not limited to, distances from two feet or less, such as 6 inches or less, including three inches or less. In one embodiment, the distance may be less than one inch from the target tissue site or organ including the target tissue. In other embodiments, the distance to the target tissue site or organ may be greater than two feet, such as up to four feet—e.g., if for instance, a tumor was present in person's extremity such as a toe and the filtration device placed in the inferior vena cava. It should be appreciated that the ranges are exemplary, and distances outside the example ranges provided are also possible.

In certain embodiments, the filtration device may be positioned in the blood vessel by inserting a catheter within the blood vessel downstream from the target tissue. In one embodiment, the filtration device is positioned within the catheter at the time the catheter is inserted within the blood vessel. In another embodiment, the catheter is first inserted within the blood vessel, and thereafter the filtration device is inserted within the lumen of the catheter. When inside the catheter, an elongated control member may be used by the operator to displace the filtration device within the lumen of the catheter until a portion of the filtration device is displaced out the distal end of the catheter and into the blood vessel. The filtration device may include a structure that expands to occupy the entire cross sectional area of the blood vessel when the structure is displaced out the distal end of the catheter.

In certain embodiments, the filtration device is removable from the catheter during use—e.g., while the catheter is still positioned inside the blood vessel. In some instances, the filtration device may be sterilized and reusable. In other instances, the filtration device may be disposable and a replacement filtration device may be inserted into the catheter after the original filtration device is discarded. The replacement filtration device is then displaced within the catheter until a portion of the replacement filtration device is displaced out the distal end of the catheter, and the filtration process repeated with the replacement filtration device.

After the filtering of the therapeutic agent is complete, the catheter may be removed from the blood vessel. In another embodiment, the catheter is removed from the blood vessel while the filtration device remains within the catheter.

The filtration device may remain in vivo for a period of time sufficient to achieve the desired reduction in level of the therapeutic agent. For example, the filtration device may be inserted into the blood vessel for a period of time of at least 5 seconds-7 days, such as, 1 minute-3 days, 10 minutes-2 days, or 30 minutes-1 day.

The filtration device may be oriented in the blood vessel such that a longitudinal axis of the device extending from a first end to a second end opposite the first end is parallel to the direction of flow of blood in the blood vessel. In certain embodiments, blood enters through a first end of the device traverses through the interior of the device and optionally around an exterior of the device and exits at an end opposite the second end. As noted herein, in certain embodiments, the wall of the device extending between the two ends of the device may include a lattice scaffold. In such embodiments, in addition to entering and exiting at ends of the device, blood may also enter and exit through the openings in the lattice wall structure.

It will be appreciated that in certain embodiments, the therapeutic agent administered to the subject is known to be therapeutically beneficial above a certain concentration level in the blood. After a certain time once the concentration decreases below a specific threshold, it is only primarily toxicity that the patient receives. In such embodiments, the present device may be placed intraarterially or intravenously at the time when the concentration drops below that agent's therapeutic level in order to filter the agent and prevent toxicity. It will be appreciated by one of skill in the art that this timing may be derivable from published known in vivo kinetics/clearance profile of the therapeutic agent.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Flow Simulation Through Filtration Devices

FIGS. 1A and 1B illustrate a side view and a top view, respectively, of a polymeric scaffold digital rendering of an exemplary filtration device.

FIGS. 2A and 2B illustrate the simulated laminar flow through an exemplary filtration device depicted in FIGS. 1A and 1B using COMSOL computational fluid dynamics. FIGS. 2A and 2B demonstrate that a filtration device as depicted in FIGS. 1A and 1B will provide for substantially laminar blood flow through the device. Laminar flow of blood through the device will have a minimal impact on rate of blood flow in the blood vessel where the filtration device is positioned and hence will not significantly affect the blood pressure.

FIGS. 3A and 3B depict a schematic of a filtration device that includes channels in honeycomb pattern. FIG. 3B demonstrates the expected flow pattern through the honeycomb channels using computational fluid dynamic (CFD) modeling. As seen in FIG. 3B, fluid flow across a honeycomb filtration device was divided among the hexagonal channels, maintaining general flow direction. Majority of the fluid traversed the channels in the center of the device. Fluid flow through the channels located towards the periphery of the device was slower than that through the centrally located hexagonal channels.

Example 2

Endovascular Filtration Devices Functionalized for Binding to Doxorubicin

Under inert atmospheric conditions at 0° C., 10.0 mL of dichloromethane ($CH_2Cl_2$) was vigorously mixed with 6.00 g of polyethylene glycol (PEG) until fully dissolved. 10 mmol of chlorosulfonic acid ($HSO_3Cl$) was added and the mixture was stirred at room temperature (20° C.) overnight to produce PEG-$SO_3$H in the form of a thick liquid. The resulting PEG-$SO_3$H was then concentrated under reduced pressure and precipitated with 25.0 mL of diethyl ether ($C_4H_{10}O$). With three additional washings with 10.0 mL of ether, the white, gummy solid of PEG-$SO_3$H was vacuum filtered. The entirety of the sulfonation of PEG reaction was done under an inert atmosphere with a nitrogen balloon and gas bubbler with silicone oil to prevent air from entering the reaction flask.

In parallel to the reaction of PEG-$SO_3$H, a 10 wt % aqueous solution of polyvinyl alcohol (PVA) was stirred at room temperature overnight. The temperature of the mixture was then raised to 90° C. for 4 hours to produce a homogeneous gel-like substance. 1 wt % of calcium chloride ($CaCl_2$) and 20 wt % of PEG-$SO_3$H were added to the PVA solution to produce an opaque gel of PEG-$SO_3$H-PVA that was of similar viscosity to honey. This soft gel was then quickly pressed into various 3D-printed molds (see e.g., FIGS. 4A, 4B, 5-7, and 14-17). To increase mechanical integrity, the resulting filtration devices were put through four full freeze/thaw cycles at −20° C. to form sulfonated cryogels of novel structures.

Figure 11:
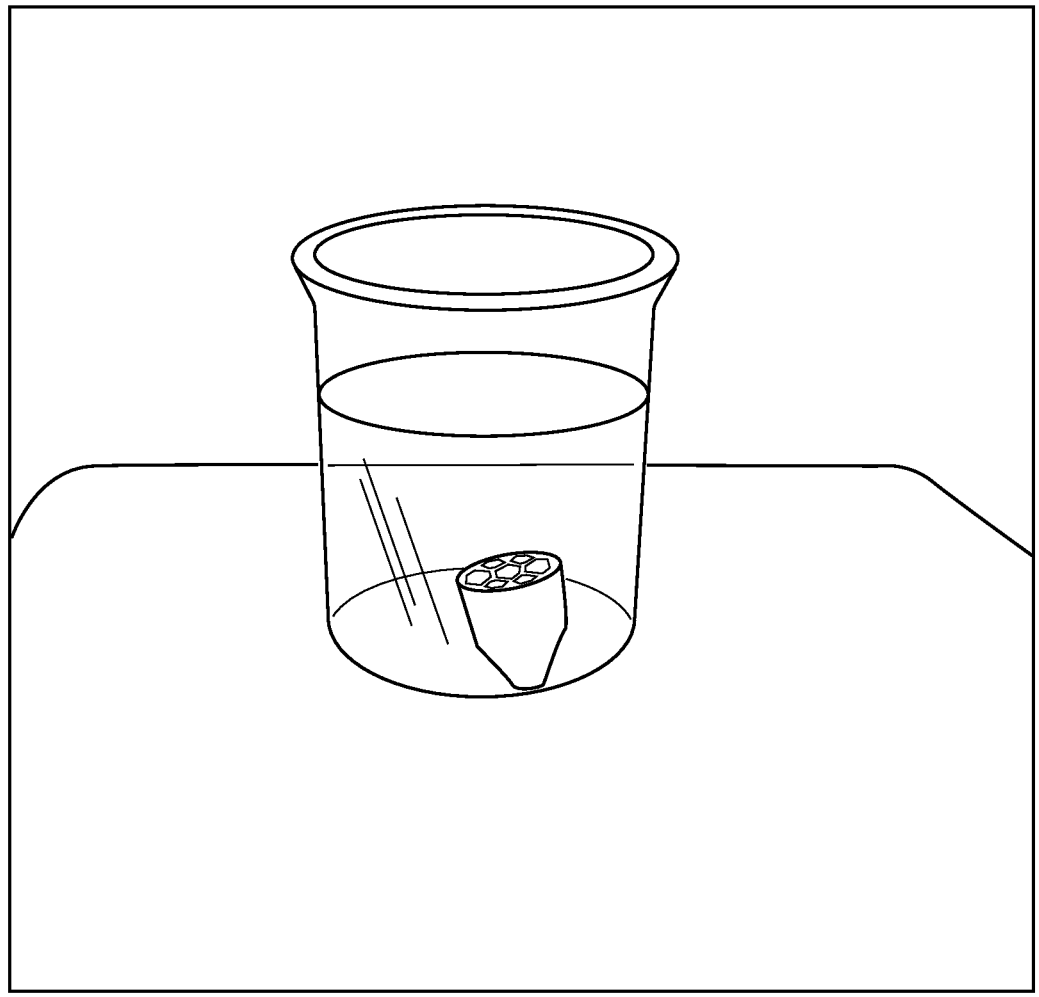
FIG. 11 illustrates an experimental setup for modeling binding of doxorubicin to an exemplary filtration device.
Figure 12:
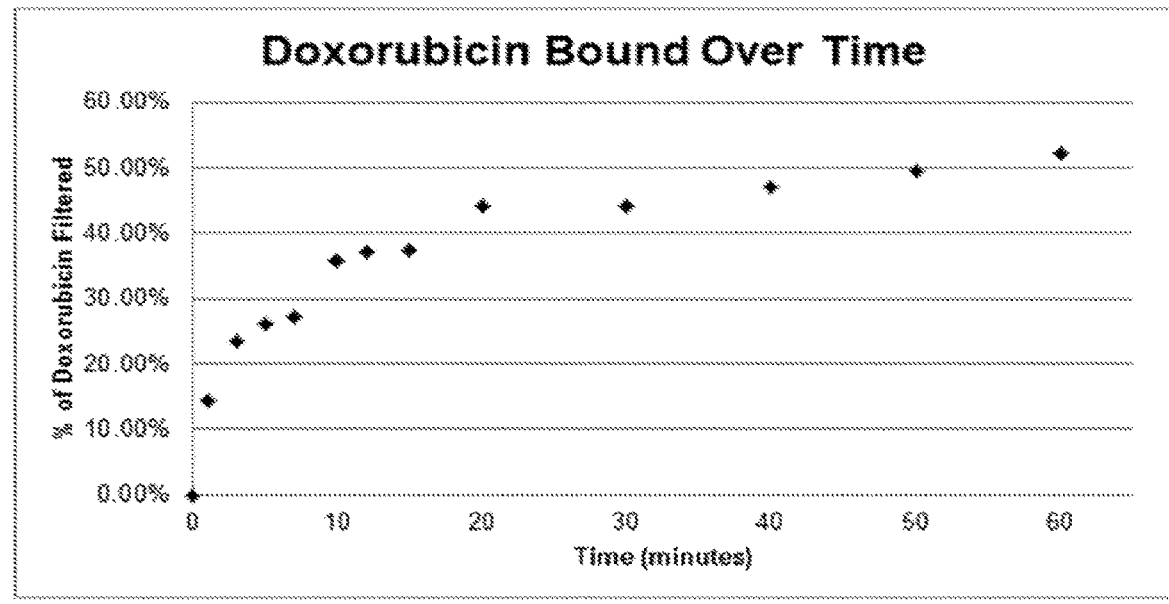
FIG. 12 illustrates a kinetic curve of the percentage of doxorubicin bound to the filtration device over time in an aqueous medium and under constant stirring using the experimental setup depicted in FIG. 11.
Figure 13:
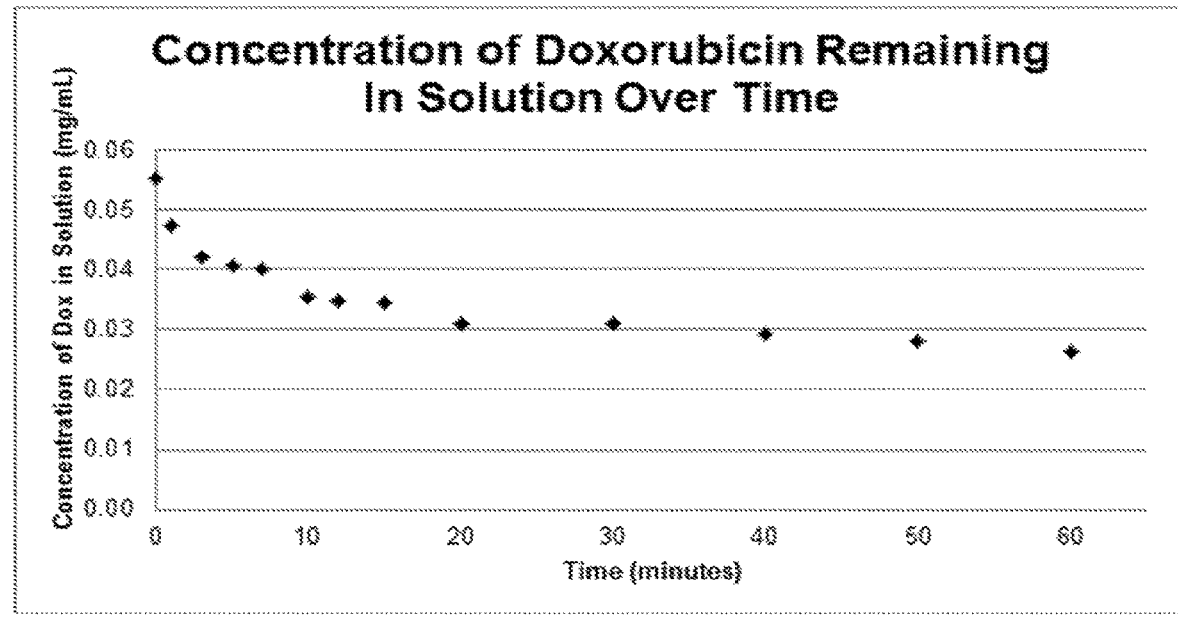
FIG. 13 illustrates a kinetic curve of the concentration of doxorubicin remaining in the aqueous medium using the experimental data obtained in FIG. 11.
Figure 14:
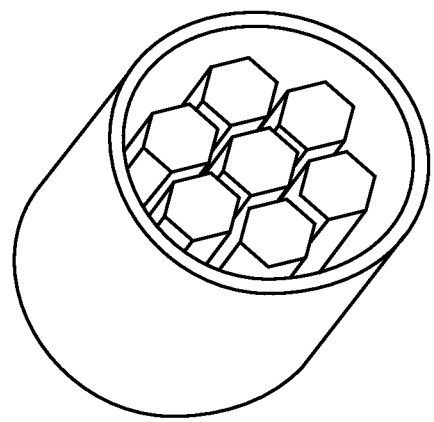
FIGS. 14-17 illustrate digital renderings of molds used in the manufacturing polymeric casting into 3D-printed negative molds.
Figure 15:
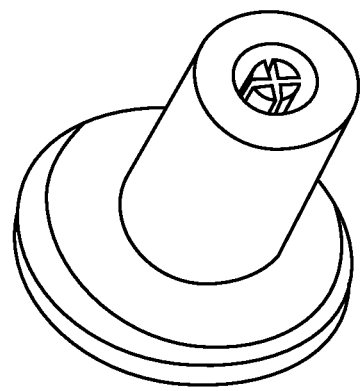
Figure 16:
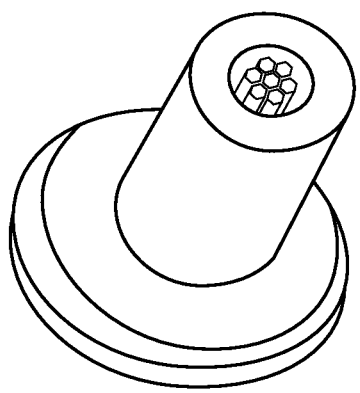
Figure 17:
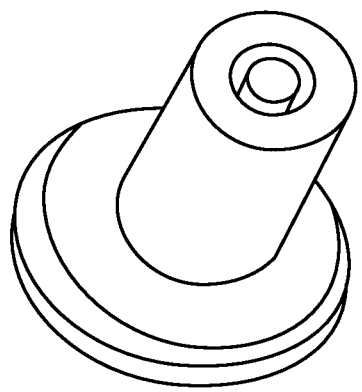
Figure 18A:
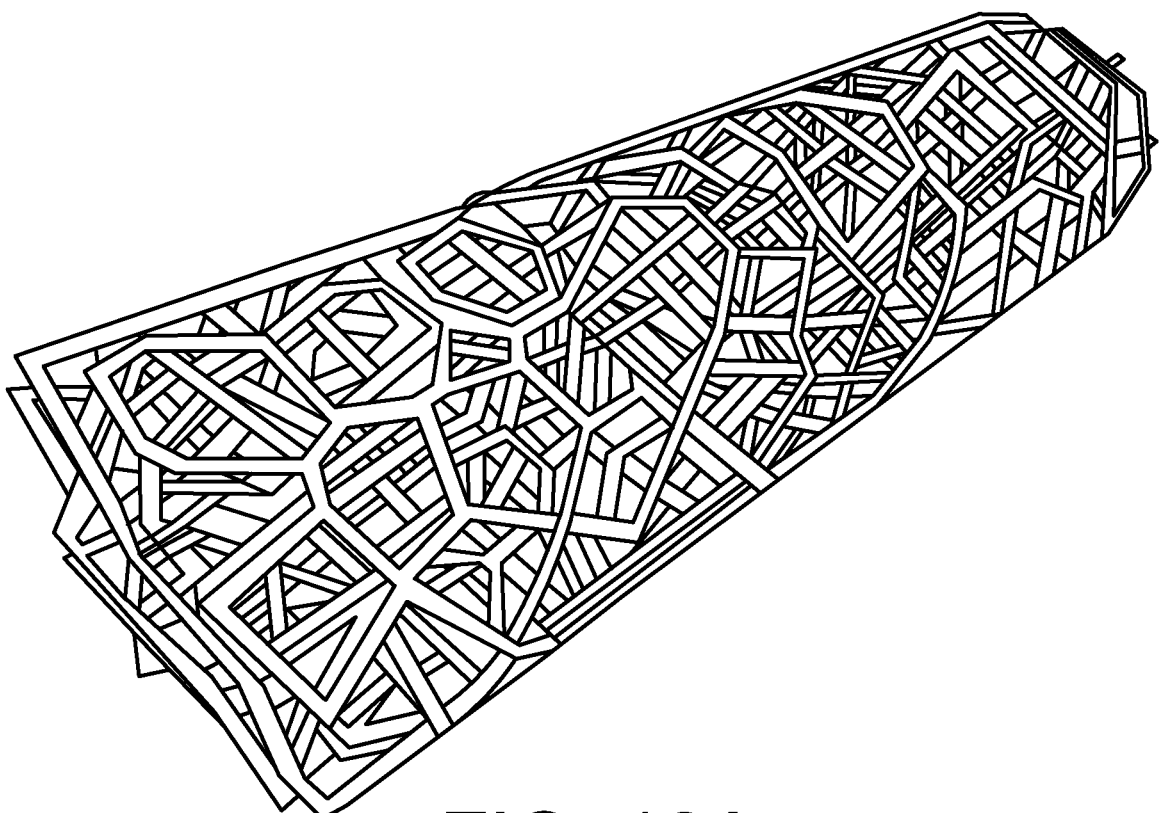
FIGS. 18A and 18B depict a filtration device with lattice scaffold that is cylindrical and tapers into a frustoconical shape.
Figure 18B:
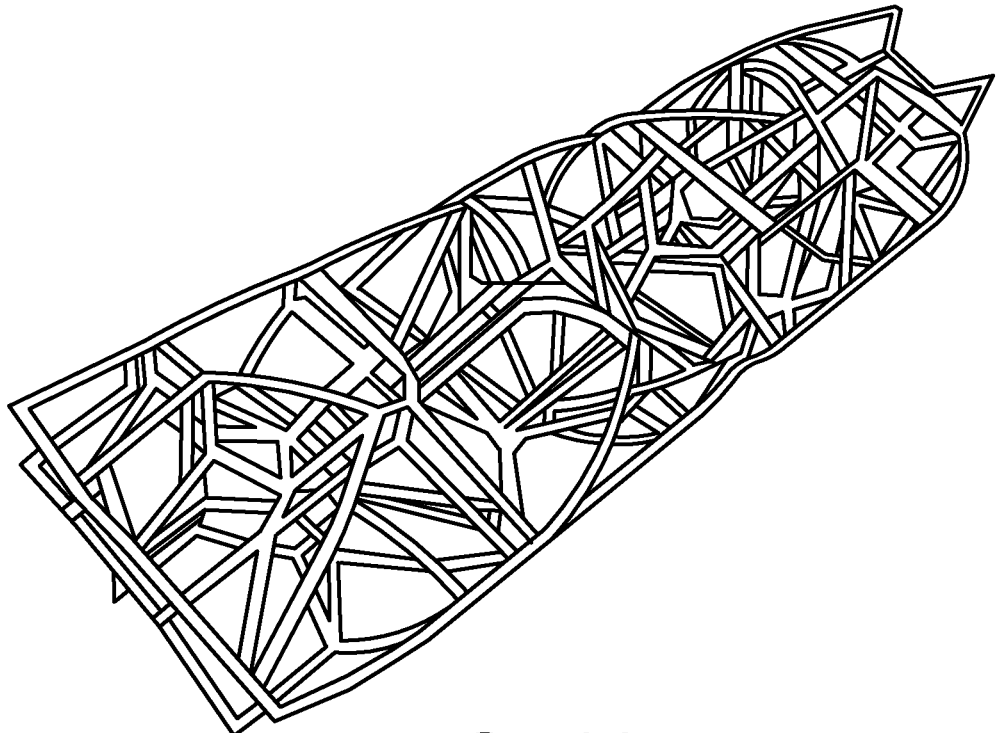
Figure 19A:
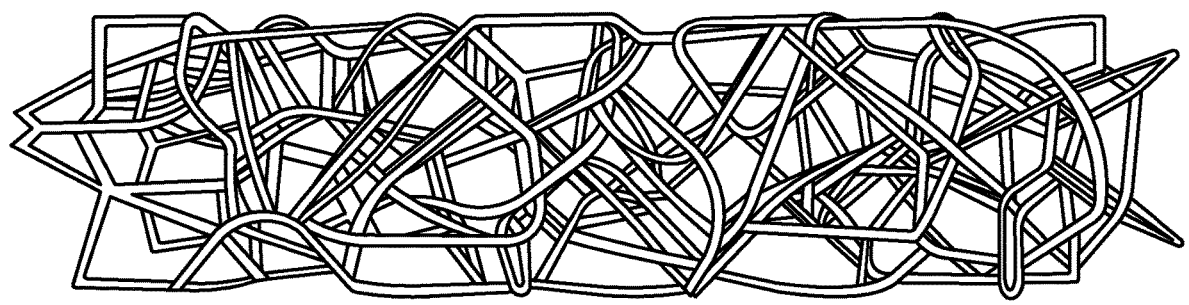
FIGS. 19A and 19B depict a filtration device with cylindrical lattice scaffold and including a cone shaped end. In the device in FIG. 19A, the cells in the lattice are uniformly sized.
Figure 19B:
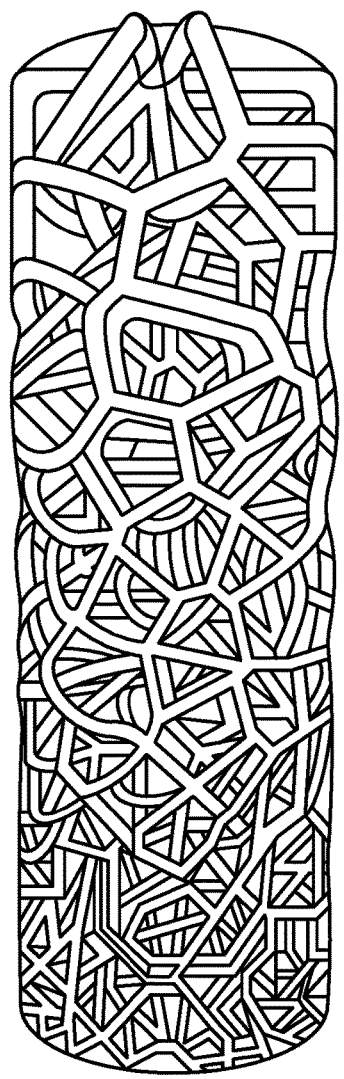
Figure 20A:
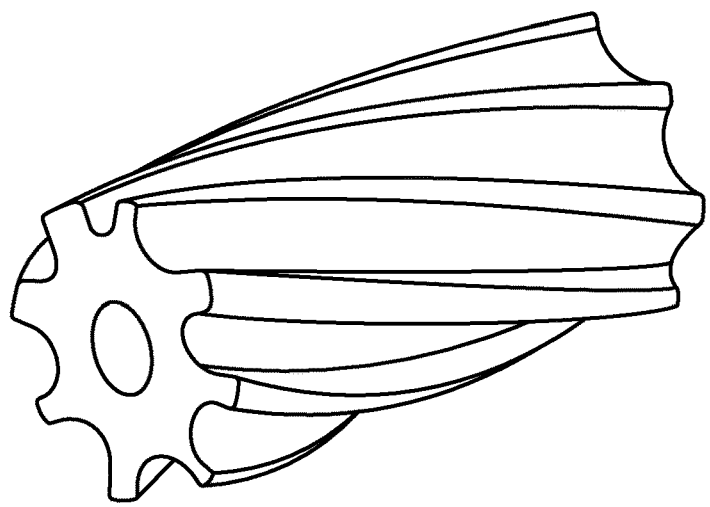
FIGS. 20A-20C illustrate solid cylindrical filtration devices having an opening at a distal planar end and another opening at the proximal planar end connected via a channel. The outer walls of the devices include a plurality of indentations that traverse from the distal planar end to the proximal planar end along a helical path. The devices in FIGS. 20A-20B differ in the pitch of the turn of the helical channels.
Figure 20B:
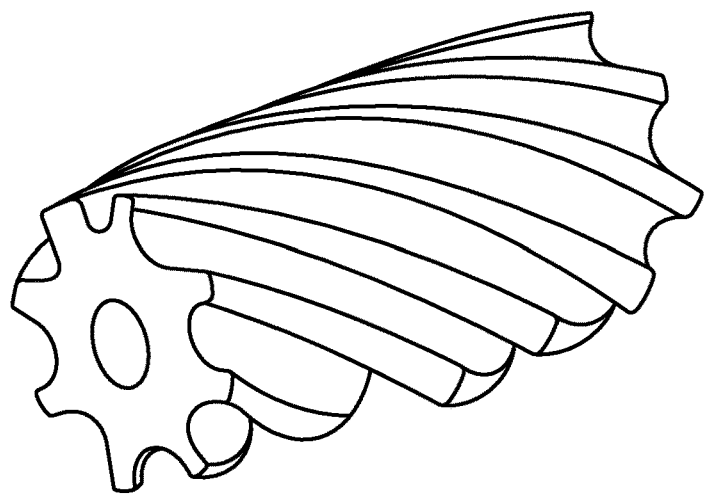
Figure 20C:
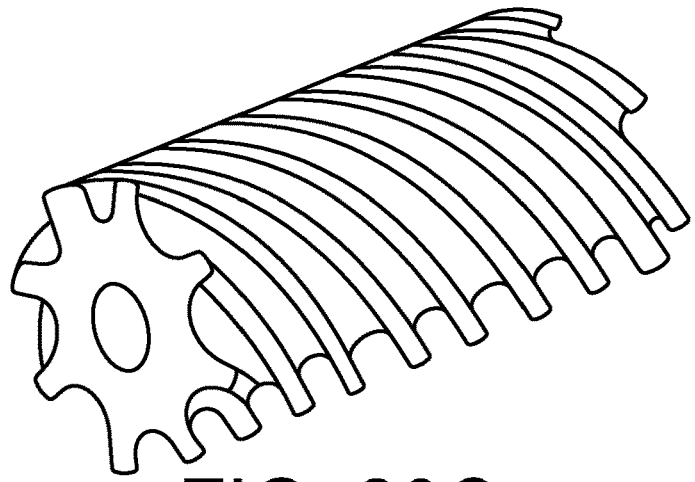
Figure 21:
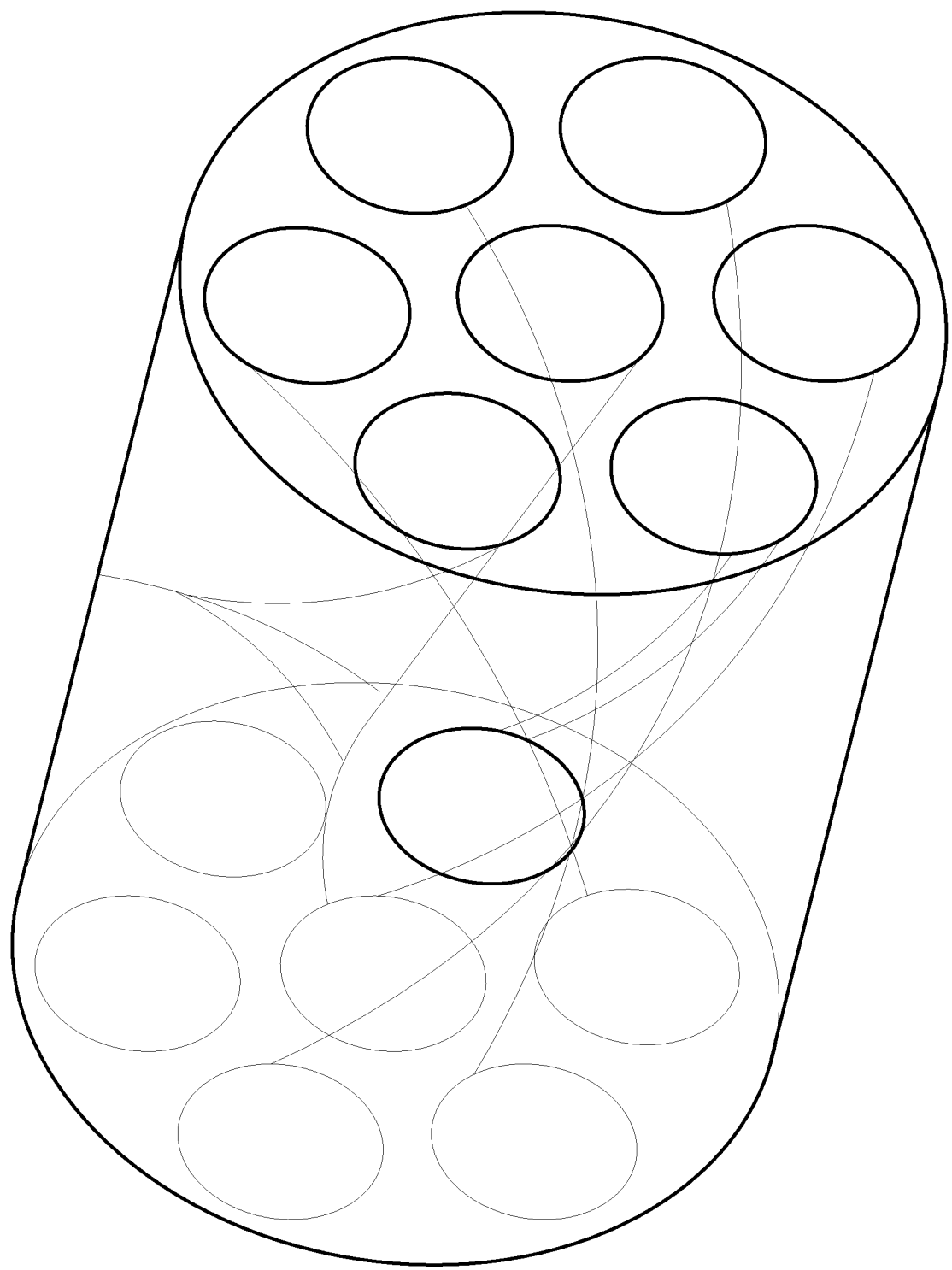
FIG. 21 depicts a solid cylindrical filtration device having a planar distal end and a planar proximal end opposite the distal end and a smooth outer wall extending between the periphery of the planar distal and planar proximal ends. The planar distal end includes a plurality of openings that are connected to openings in the planar proximal end via circular channels that are disposed helically.
Figure 22A:
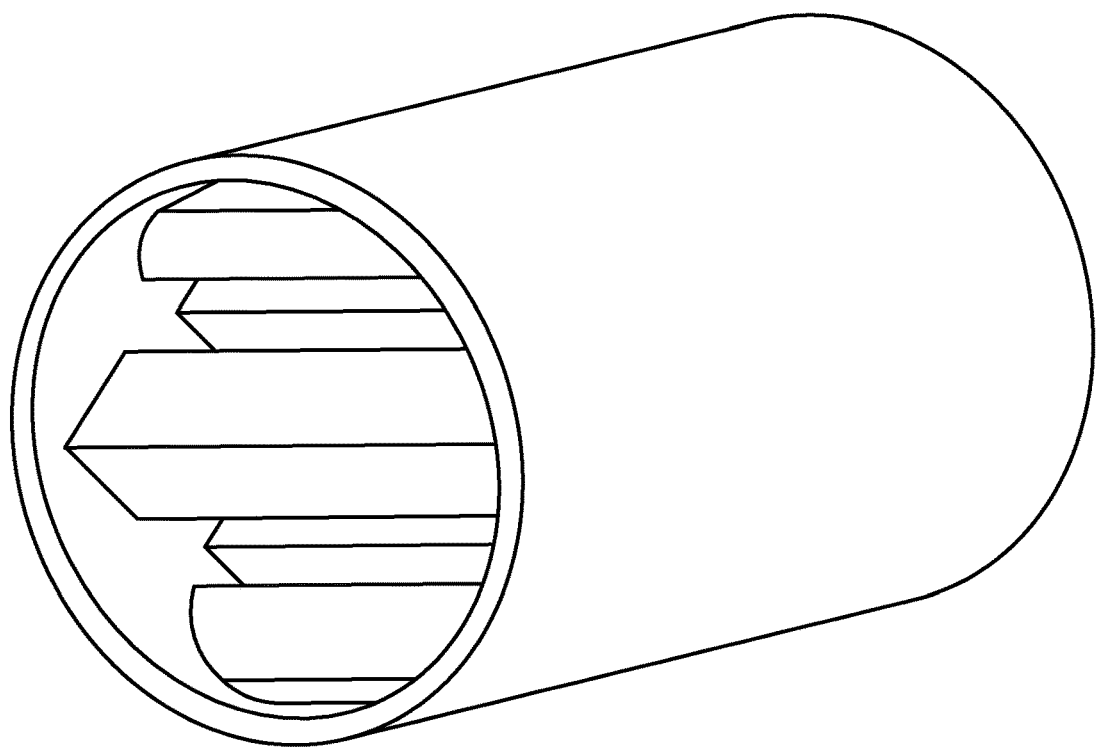
FIGS. 22A and 22B illustrate a hollow cylindrical filtration device with a smooth outer wall and a plurality of cuboid shaped struts extending from a first location in the inner wall of the device to second location in the inner wall opposite the first location.
Figure 22B:
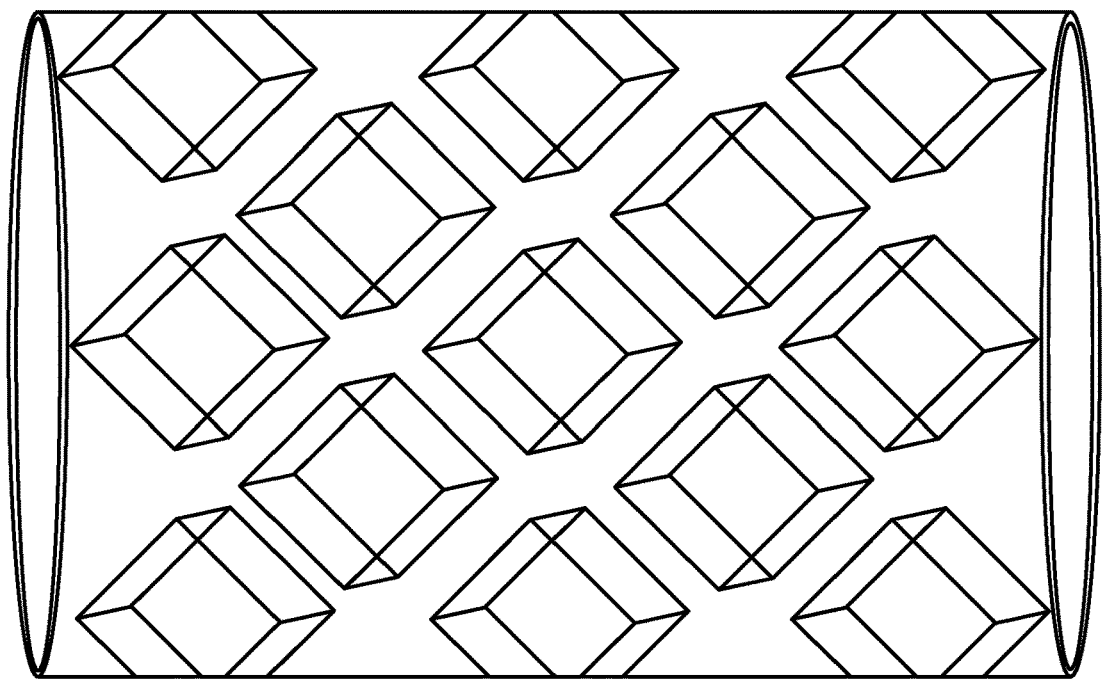
Figure 23A:
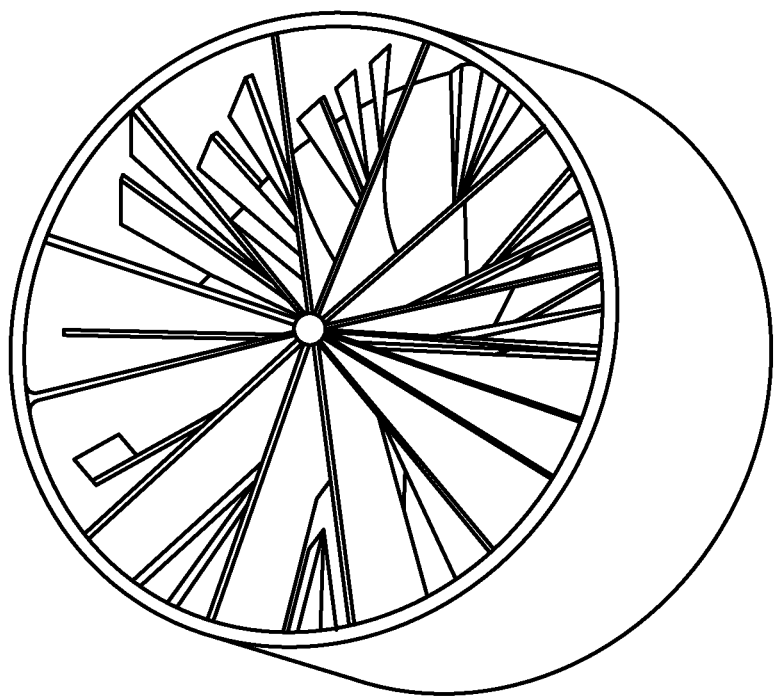
FIG. 23A-23E show different view of a hollow cylindrical filtration device with the interior housing a plurality of blade shaped structure arranged like blades in a turbine.
Figure 23B:
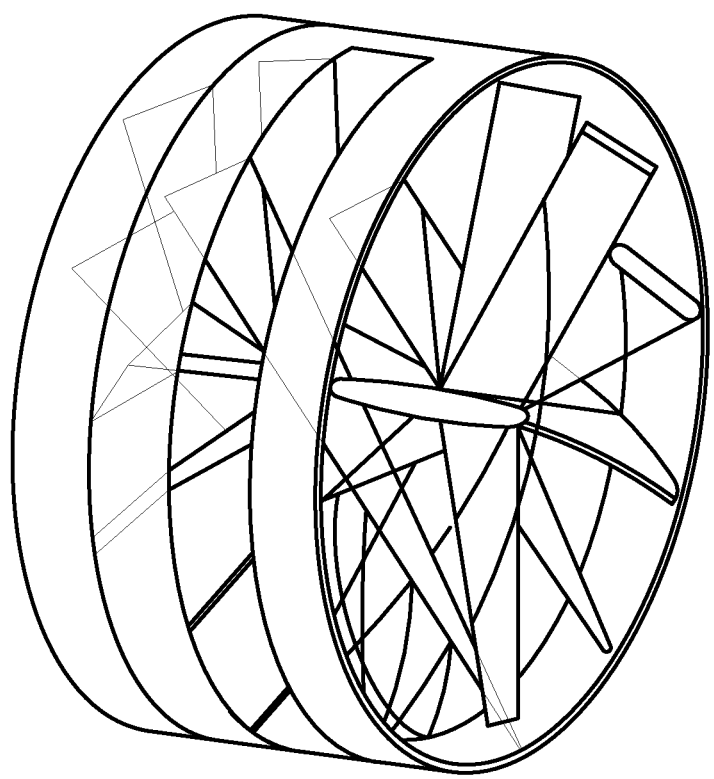
Figure 23C:
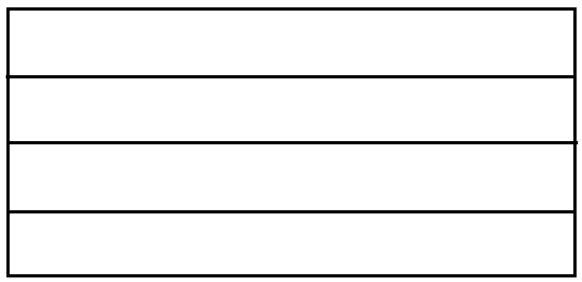
Figure 23D:
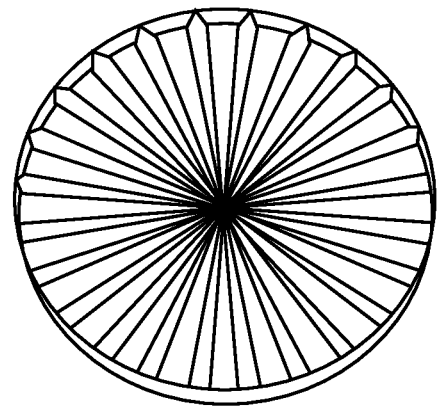
Figure 23E:
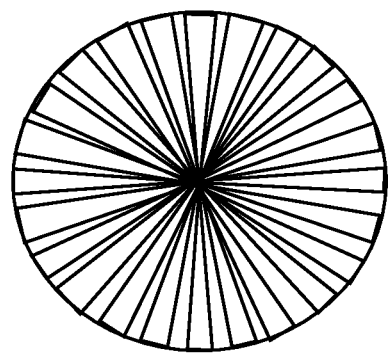
Figure 24A:
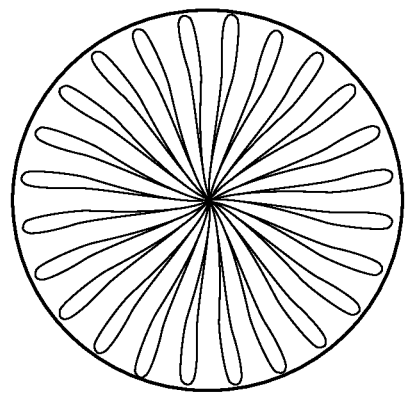
FIGS. 24A-24E are different embodiments of the same device as shown in FIGS. 24A-24E, with the inner turbine-like blades swept 30° distally.
Figure 24B:
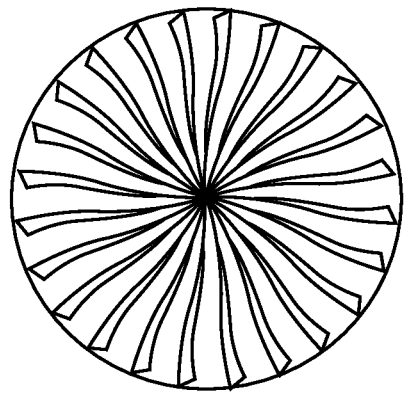
Figure 24C:
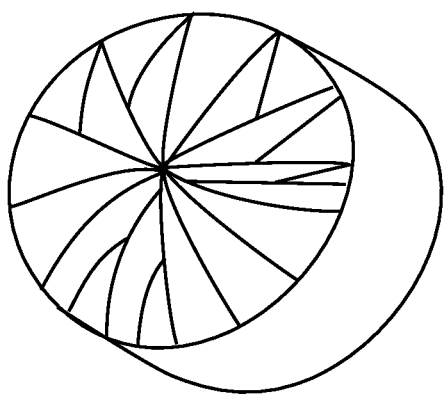
Figure 24D:
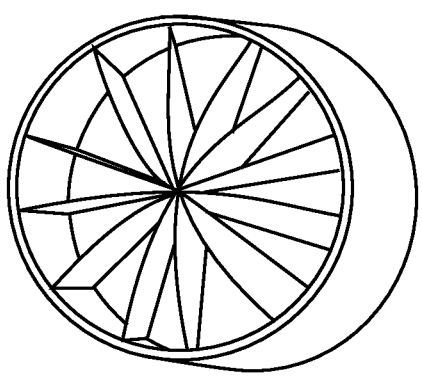
Figure 24E:
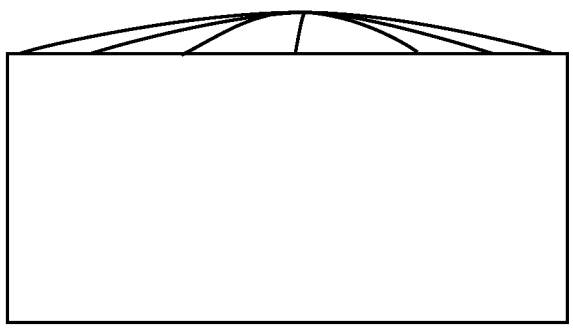
Figure 25A:
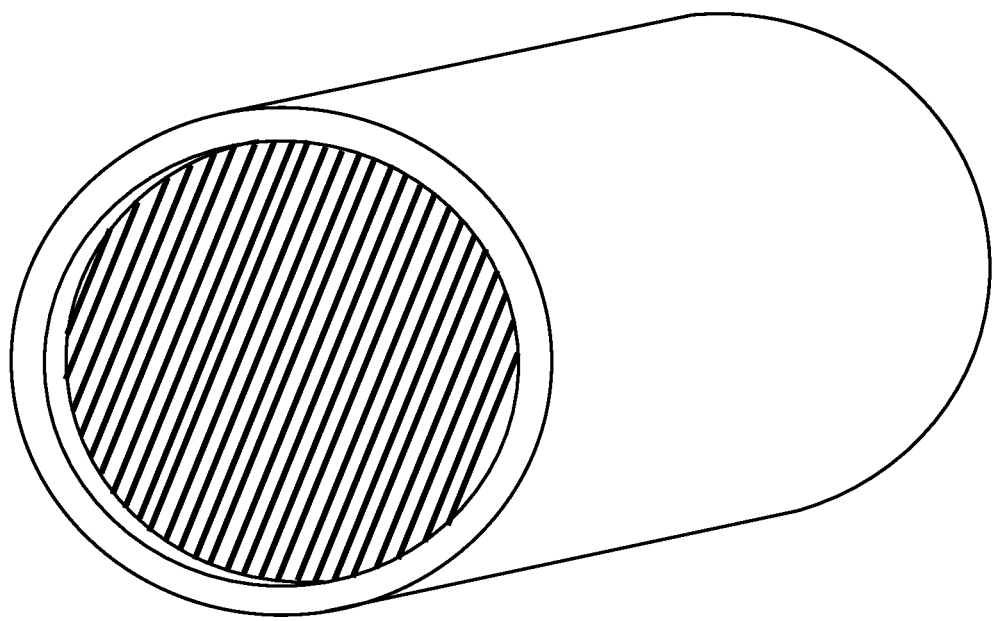
FIGS. 25A-25D depict cylindrical filtration devices with a plurality of vent shaped structures traversing across the interior of the device. The vents are arranged parallel to each other and extend straight from the between two ends of the device in FIG. 25A.
Figure 25B:
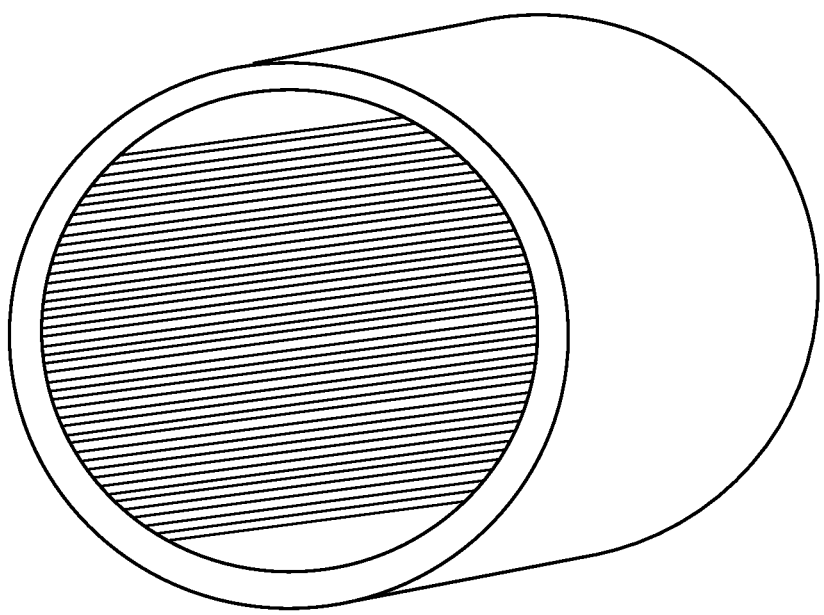
Figure 25C:
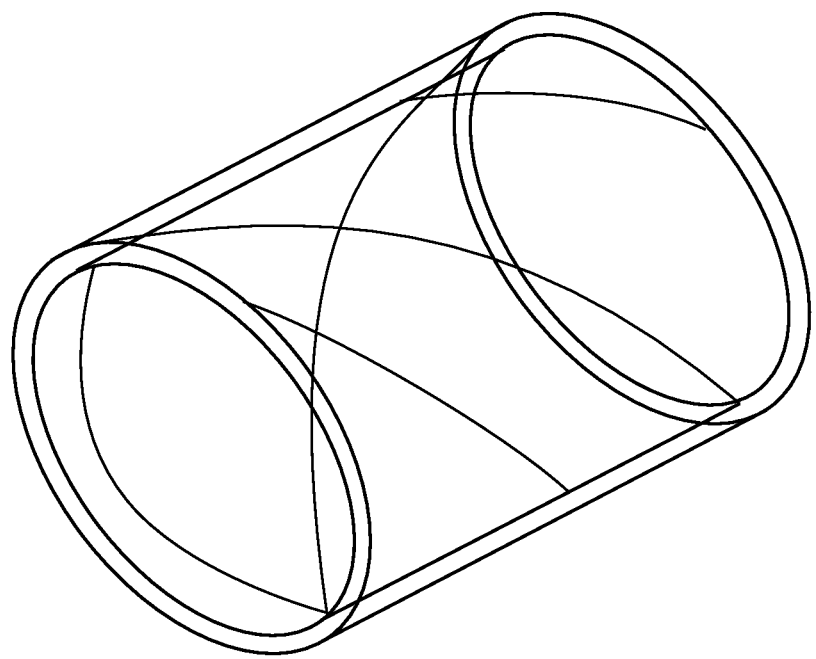
Figure 25D:
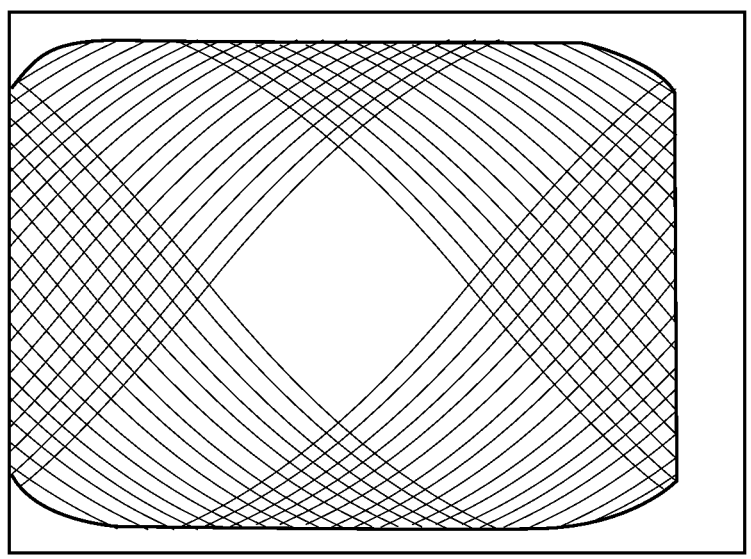

In an alternate procedure, a 10 wt % aqueous solution of PVA was stirred at ambient temperature for 24 hours. Upon raising the temperature to completely homogenize the solution, 60% (v/v) of 4-Sulfophthalic acid solution was added drop-wise under constant magnetic stirring. The temperature was lowered to ambient, and the resulting honey-like mixture was stirred for 24 hours to allow the Sulfonation reaction to come to completion. An aqueous solution of glutaraldehyde was added to the resulting viscous polymer and it was then casted into negative mold. Then, they underwent 3 freeze/thaw cycles between −20° C. and ambient temperatures. After cryogelation, gels were removed from their respective molds to continue on with doxorubicin testing. Gels were immersed in an aqueous solution of 0.025 mg/mL of doxorubicin (FIG. 11). Samples of the solution were taken at time points (in minutes) of t=0, 5, 10, 20, 30, 45, 60, 90, and 120. Absorbance of these samples were measured at a 480 nm wavelength, and was used to calculate their corresponding concentrations of doxorubicin. The resulting $SO_3$H-PVA copolymer was able to bind to doxorubicin over time (see FIGS. 12-13).

Resulting copolymers showed excellent mechanical properties and structural memory. Preliminary-crush testing validated that synthesized PVA gels have structural memory. PVA gels formed after cryogelation (using freezing to induce polymerization) are able to be crushed to 50% of their original diameter and return to their original shape without any deformation.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A filtration device for filtering one or more therapeutic agents in blood flowing in a blood vessel, the filtration device comprising:
   an elongate control member;
   a solid elongated member having a proximal end and a distal end carried on the control member such that the control member may be used to displace the solid elongated member out a distal end of a catheter;
   a plurality of channels formed in the solid elongated member, wherein the plurality of channels are parallel to each other and extend from the proximal end to the distal end along a longitudinal axis of the solid elongated member;
   wherein the filtration device is dimensioned for positioning within a blood vessel of a human or non-human animal; and
   wherein surfaces of the channels are functionalized to bind to a therapeutic agent in blood flowing through the channels.

2. The filtration device according to claim 1, wherein the solid elongated member comprises a cylindrical member comprising a frustoconical leading edge opposite a planar edge;
   the plurality of channels formed in the solid elongated member, wherein the channels extend from the frustoconical leading edge to the planar edge.

3. The filtration device according to claim 1, wherein the solid elongated member is a cylindrical member comprising a first planar edge opposite a second planar edge and the plurality of channels extend from the first planar edge to the second planar edge.

4. The filtration device according to claim 1, wherein a channel of the plurality of channels is located in the center of the device and remaining plurality of channels are arranged concentrically around the central channel.

5. The filtration device according to claim 1, wherein the solid elongated member is cylindrical and is dimensioned to (a) fill a cross-section of the blood vessel, (b) have a diameter smaller than the blood vessel diameter, or (c) have a diameter larger than the blood vessel diameter.

6. The filtration device according to claim 1, wherein a surface of the device at one or more edges and the surfaces of the plurality of channels of the device are functionalized to bind to a first therapeutic agent or to a plurality of therapeutic agents.

7. The filtration device according to claim 1, wherein the plurality of channels comprise a circular or an oval shaped opening at an edge of the device.

8. The filtration device according to claim 1, wherein the plurality of channels comprise a hexagonal opening at an edge of the device.

9. The filtration device according to claim 1, wherein the periphery of the plurality of channels comprise a hexagonal shape along the length of the channels.

10. The filtration device according to claim 1, wherein the periphery of the plurality of channels comprise a cylindrical shape along the length of the channels.

11. The filtration device according to claim 1, wherein the outer surface of the device and the interior surface of the channels is functionalized with a moiety for binding to a first therapeutic agent.

12. The filtration device according to claim 1, wherein the outer surface of the device and/or the interior surface of the channels is functionalized with a plurality of moieties for binding to a plurality of therapeutic agents.

13. A method for filtering a therapeutic agent from blood, the method comprising:
   inserting a distal end of a catheter within a blood vessel downstream from a target tissue site;
   positioning the filtration device of claim 1 within a lumen of the catheter;
   displacing the filtration device at least partially out the distal end of the catheter to position the filtration device downstream from the target tissue site in the blood vessel; and
   administering a therapeutic agent upstream from the target tissue site to direct flow of the therapeutic agent to the target tissue site and then to the filtration device;
   wherein the in vivo positioned filtration device binds the therapeutic agent as the blood containing the therapeutic agent traverses through the channels of the filtration device.

14. The method according to claim 13, further comprising:
   removing the filtration device from the blood vessel of the body of the human or non-human animal after a completion of the filtering of the therapeutic agent.

15. The method according to claim 14, further comprising:
   inserting a replacement filtration device within the catheter;
   displacing the replacement filtration device at least partially out the distal end of the catheter to position the replacement filtration device downstream from the target tissue site in the blood vessel.

16. The method according to claim 13, wherein the filtration device is positioned 10 mm to 1000 mm downstream from the target tissue site.

17. The method according to claim 13, wherein the catheter is positioned concentrically around the filtration device when the catheter is inserted within the blood vessel.

18. The method according to claim 13, wherein the filtration device is positioned within the vein draining the target tissue site.

19. The method according to claim 13, wherein the filtration device is positioned via an internal jugular or femoral vein.

20. The method according to claim 13, wherein the solid elongated member comprises a cylindrical member comprising a frustoconical leading edge opposite a planar edge; a plurality of channels formed in the solid elongated member, wherein the channels extend from the frustoconical leading edge to the planar edge, wherein the filtration device is positioned in the blood vessel such that the blood enters the filtration device at the frustoconical leading edge and exits the device at the planar edge.

21. The method according to claim 13, wherein a first channel of the plurality of channels is located in the center of the device and extends from the frustoconical edge to the planar edge and remaining plurality of channels are arranged concentrically around the central channel.

22. The method according to claim 13, wherein the cylindrical member is dimensioned to fill a cross-section of the blood vessel such that the longitudinal axis is parallel to the direction of flow of blood in the blood vessel such that the blood traverses through the channels of the device.

23. The method according to claim 13, wherein a surface of the plurality of channels of the device is functionalized to bind to one or more therapeutic agents.

24. The method according to claim 13, wherein the plurality of channels comprise a circular or oval opening at the frustoconical leading edge.

25. The method according to claim 13, wherein the solid elongated member is a cylindrical member comprising a first planar edge opposite a second planar edge and a plurality of channels extending from the first planar edge to the second planar edge, the plurality of channels comprising a circular opening at the planar edge.

26. The method according to claim 25, wherein the channels comprise a hexagonal opening at the first and second planar edge.

27. The method according to claim 13, wherein the periphery of the plurality of channels comprises a hexagonal shape along the length of the channels.

28. The method according to claim 13, wherein the periphery of the plurality of channels comprises a cylindrical shape along the length of the channels.

29. The method according to claim 13, wherein the interior surface of the channels is functionalized with a first moiety for binding to a first therapeutic agent.

30. The method according to claim 13, wherein the interior surface of the channels is functionalized with a plurality of moieties for binding to a plurality of therapeutic agents.

31. The method according to claim 13, wherein the solid elongated member comprises a cylindrical member comprising a frustoconical leading edge opposite a planar edge; a plurality of channels formed in the solid elongated member, wherein the channels extend from the frustoconical leading edge to the planar edge and are hexagonal in shape and parallel the longitudinal axis of the device.

32. The method according to claim 13, wherein the solid elongated member expands within the blood vessel when displaced out the distal end of the catheter.

33. The method according to claim 13, wherein the therapeutic agent is a chemotherapeutic agent, antibiotics, or a thrombolytic.

34. The method according to claim 33, wherein the chemotherapeutic agent is one or more of doxorubicin, cyclophosphamide, methotrexate, 5-fluorouracil, vincristine, cisplatin, and epirubicin.

35. The filtration device according to claim 1, wherein the solid elongated member comprises a biocompatible-polymer-casted scaffold.

36. The filtration device according to claim 1, wherein the solid elongated member comprises a structure configured to expand within the blood vessel when the structure is displaced out the distal end of the catheter.

37. A system for filtering one or more therapeutic agents in blood flowing in a blood vessel, the filtration device comprising:
 a catheter comprising a lumen and a distal end sized for introduction into a blood vessel downstream from a target tissue site;
 a filtration device comprising a solid elongated member having a proximal end and a distal end, a plurality of channels formed in the solid elongated member that extend substantially parallel to each other between the proximal end and the distal end of the solid elongated member; and
 an elongated control member carrying the filtration device such that the control member may be used to displace the solid elongated member out a distal end of a catheter within the blood vessel downstream from the target tissue site,
 wherein surfaces of the channels are functionalized to bind to a therapeutic agent in blood flowing through the channels.

38. The system according to claim 37, wherein the solid elongated member comprises a structure configured to expand within the blood vessel when the structure is displaced out the distal end of the catheter.

39. The system according to claim 38, wherein the structure is configured to expand to occupy the entire cross-sectional area of the blood vessel to direct blood flowing through the blood vessel through the channels.

40. The system according to claim 38, wherein the plurality of channels are configured to extend substantially parallel to a longitudinal axis of the device when the structure expands.

* * * * *